(12) United States Patent
Wondka et al.

(10) Patent No.: US 10,034,621 B2
(45) Date of Patent: Jul. 31, 2018

(54) COLLECTION AND ANALYSIS OF A VOLUME OF EXHALED GAS WITH COMPENSATION FOR THE FREQUENCY OF A BREATHING PARAMETER

(71) Applicant: Capnia, Inc., Palo Alto, CA (US)

(72) Inventors: Anthony D. Wondka, San Ramon, CA (US); Anish Bhatnagar, Redwood City, CA (US)

(73) Assignee: Capnia, Inc., Redwood City, CA (US)

( * ) Notice: Subject to any disclaimer, the term of this patent is extended or adjusted under 35 U.S.C. 154(b) by 724 days.

(21) Appl. No.: 13/722,950

(22) Filed: Dec. 20, 2012

(65) Prior Publication Data

US 2013/0165806 A1 Jun. 27, 2013

Related U.S. Application Data

(60) Provisional application No. 61/578,811, filed on Dec. 21, 2011.

(51) Int. Cl.
*A61B 5/08* (2006.01)
*A61B 5/097* (2006.01)
(Continued)

(52) U.S. Cl.
CPC .............. *A61B 5/097* (2013.01); *A61B 5/082* (2013.01); *A61B 5/0816* (2013.01);
(Continued)

(58) Field of Classification Search
None
See application file for complete search history.

(56) References Cited

U.S. PATENT DOCUMENTS 2,073,192 A 3/1937 Connell
3,306,283 A 2/1967 Arp
(Continued)

FOREIGN PATENT DOCUMENTS

CN 101214151 A 7/2008
CN 101366672 A 2/2009
(Continued)

OTHER PUBLICATIONS

International Search Report and Written Opinion for PCT/US12/71085, dated May 13, 2013, 10 pages.
(Continued)

*Primary Examiner* — Etsub Berhanu
(74) *Attorney, Agent, or Firm* — Cooley LLP

(57) ABSTRACT

Apparatuses are described to accurately determine a gas concentration of a sample of a patient's breath. The apparatuses may include a sample compartment, a breath speed analyzer, a gas analyzer, and a processor. The sample compartment includes an inlet that receives the breath. The breath speed analyzer determines the speed of a portion of the breath. The gas analyzer determines a gas concentration. The processor includes an algorithm that determines a degree of non-homogeneity of the sample based on the speed, and a corrected gas concentration based on the degree of non-homogeneity. In some variations, the gas correction is determined independently of patient cooperation. Apparatuses may be tuned based on the intended population's expected breathing pattern ranges such that the sample compartment is filled with a homogenous end-tidal gas sample regardless of an individual's breathing pattern. These apparatuses are useful, for example, for end-tidal CO analysis. Methods are also described.

8 Claims, 20 Drawing Sheets

(51) Int. Cl.
*A61B 5/00* (2006.01)
*A61B 5/083* (2006.01)
(52) U.S. Cl.
CPC .......... *A61B 5/0836* (2013.01); *A61B 5/7225* (2013.01); *A61B 5/7285* (2013.01); *A61B 5/7292* (2013.01)

(56) References Cited

U.S. PATENT DOCUMENTS

| | | | |
|---|---|---|---|
| 3,343,529 A | 9/1967 | Miller et al. | |
| 3,858,573 A | 1/1975 | Ryan et al. | |
| 3,910,261 A | 10/1975 | Ragsdale et al. | |
| 4,440,177 A | 4/1984 | Anderson et al. | |
| 4,619,269 A | 10/1986 | Cutlet et al. | |
| 5,003,985 A | 4/1991 | White et al. | |
| 5,069,220 A | 12/1991 | Casparie et al. | |
| 5,072,737 A | 12/1991 | Goulding | |
| 5,129,401 A | 7/1992 | Corenman et al. | |
| 5,285,794 A | 2/1994 | Lynch | |
| 5,357,971 A | 10/1994 | Sheehan et al. | |
| 5,361,771 A | 11/1994 | Craine et al. | |
| 5,361,772 A | 11/1994 | Murnick et al. | |
| 5,363,857 A | 11/1994 | Howard | |
| 5,383,469 A | 1/1995 | Vreman et al. | |
| 5,533,512 A | 7/1996 | Novotny et al. | |
| 5,533,513 A | 7/1996 | Ueda et al. | |
| 5,573,005 A | 11/1996 | Ueda et al. | |
| 5,924,995 A | 7/1999 | Klein et al. | |
| 5,971,934 A | 10/1999 | Scherer et al. | |
| 6,010,459 A | 1/2000 | Silkoff et al. | |
| 6,251,082 B1 | 6/2001 | Rayburn | |
| 6,278,975 B1 | 8/2001 | Brant et al. | |
| 6,428,483 B1 | 8/2002 | Carlebach | |
| 6,544,190 B1 | 4/2003 | Smits et al. | |
| 6,582,376 B2 | 6/2003 | Baghdassarian | |
| 6,620,107 B2 | 9/2003 | Payne et al. | |
| 6,733,463 B2 | 5/2004 | Moilanen et al. | |
| 6,739,335 B1 | 5/2004 | Rapport et al. | |
| 6,799,575 B1 | 10/2004 | Carter | |
| 7,063,667 B1 | 6/2006 | Ben-Oren et al. | |
| 7,191,000 B2 | 3/2007 | Zhu et al. | |
| 7,223,244 B1 | 5/2007 | Koh | |
| 7,600,439 B1 | 10/2009 | Patterson et al. | |
| 8,021,308 B2 | 9/2011 | Capnia | |
| 8,251,914 B2 | 8/2012 | Daniels et al. | |
| 8,485,984 B2 | 7/2013 | Giron et al. | |
| 8,679,029 B2 | 3/2014 | Krauss et al. | |
| 2001/0037070 A1 | 11/2001 | Cranley et al. | |
| 2002/0138213 A1 | 9/2002 | Mault | |
| 2002/0151814 A1 | 10/2002 | Payne et al. | |
| 2003/0008407 A1 | 1/2003 | Fu | |
| 2003/0191405 A1 | 10/2003 | Rich et al. | |
| 2003/0208133 A1* | 11/2003 | Mault ................ | A61B 5/0002 600/532 |
| 2004/0077995 A1* | 4/2004 | Ferek-Petric ........... | A61M 5/14 604/66 |
| 2004/0210154 A1 | 10/2004 | Kline | |
| 2005/0137491 A1* | 6/2005 | Paz ..................... | A61B 5/097 600/543 |
| 2005/0177056 A1 | 8/2005 | Giron et al. | |
| 2006/0094964 A1* | 5/2006 | Ragauskas ............. | A61B 5/08 600/454 |
| 2006/0133960 A1 | 6/2006 | Ahmad | |
| 2006/0178592 A1 | 8/2006 | Nason et al. | |
| 2006/0195040 A1 | 8/2006 | Nason et al. | |
| 2006/0200037 A1 | 9/2006 | Falasco | |
| 2006/0241507 A1 | 10/2006 | Carlson et al. | |
| 2007/0073182 A1* | 3/2007 | Wilson ................. | A61B 5/083 600/532 |
| 2007/0129647 A1 | 6/2007 | Lynn | |
| 2007/0167853 A1 | 7/2007 | Melker et al. | |
| 2007/0173731 A1 | 7/2007 | Meka et al. | |
| 2007/0261472 A1 | 11/2007 | Flaherty et al. | |
| 2008/0009762 A1 | 1/2008 | Hampton et al. | |
| 2008/0119753 A1 | 5/2008 | Ricciardelli et al. | |
| 2008/0121230 A1 | 5/2008 | Cortez et al. | |
| 2009/0044805 A1 | 2/2009 | Somaiya et al. | |
| 2009/0187113 A1 | 7/2009 | Friedman et al. | |
| 2009/0246891 A1 | 10/2009 | Sato et al. | |
| 2009/0247891 A1* | 10/2009 | Wood ..................... | A61B 5/083 600/532 |
| 2010/0317986 A1 | 12/2010 | Colman et al. | |
| 2011/0004108 A1 | 1/2011 | Peyton | |
| 2011/0021942 A1 | 1/2011 | Choe et al. | |
| 2011/0066060 A1 | 3/2011 | Von Bahr et al. | |
| 2011/0196295 A1 | 8/2011 | Gonzalez et al. | |
| 2011/0257550 A1 | 10/2011 | Choi | |
| 2011/0263947 A1 | 10/2011 | Utley et al. | |
| 2012/0055481 A1 | 3/2012 | Orr et al. | |
| 2012/0090378 A1 | 4/2012 | Wang et al. | |
| 2012/0215125 A1 | 8/2012 | Orr et al. | |
| 2012/0247471 A1 | 10/2012 | Masic et al. | |
| 2012/0302908 A1 | 11/2012 | Hemnes et al. | |
| 2012/0310104 A1 | 12/2012 | Van Kesteren et al. | |
| 2013/0165806 A1 | 6/2013 | Wondka et al. | |
| 2013/0217029 A1 | 8/2013 | Sislian et al. | |
| 2013/0267862 A1 | 10/2013 | Jaffe et al. | |
| 2014/0194703 A1 | 7/2014 | Wondka et al. | |
| 2014/0228699 A1 | 8/2014 | Causevic | |
| 2015/0065900 A1 | 3/2015 | Wondka et al. | |
| 2015/0065901 A1 | 3/2015 | Bhatnagar et al. | |
| 2015/0265184 A1 | 9/2015 | Wondka et al. | |
| 2016/0106343 A1 | 4/2016 | Wondka et al. | |

FOREIGN PATENT DOCUMENTS

| | | |
|---|---|---|
| CN | 101547716 A | 9/2009 |
| CN | 101636109 A | 1/2010 |
| CN | 102770069 A | 11/2012 |
| EP | 0 574 027 A2 | 12/1993 |
| EP | 0 648 088 | 4/1995 |
| EP | 1 480 557 | 12/2004 |
| EP | 0892926 | 12/2006 |
| EP | 2 066 236 A2 | 6/2009 |
| EP | 2293056 | 3/2011 |
| EP | 1850748 | 8/2011 |
| EP | 1850748 B1 | 8/2011 |
| GB | 2472116 | 1/2011 |
| JP | S-49-009085 A | 1/1974 |
| JP | S-61-100231 A | 5/1986 |
| JP | H-7-116145 A | 5/1995 |
| JP | 2003-529044 A | 9/2003 |
| JP | 2005-519272 A | 6/2005 |
| JP | 2009-058398 A | 3/2009 |
| WO | WO-97/43952 A1 | 11/1997 |
| WO | WO-00/063683 A1 | 10/2000 |
| WO | WO-03/073935 A2 | 9/2003 |
| WO | WO-03/073935 A3 | 9/2003 |
| WO | WO-2004/032719 A2 | 4/2004 |
| WO | WO-2004/032719 A3 | 4/2004 |
| WO | WO-2007/059263 A2 | 5/2007 |
| WO | WO-2007/059263 A3 | 5/2007 |
| WO | WO-2008/019680 A2 | 2/2008 |
| WO | WO-2008/019680 A3 | 2/2008 |
| WO | WO-2008/060165 A1 | 5/2008 |
| WO | WO-2008/081449 A2 | 7/2008 |
| WO | WO-2008/081449 A3 | 7/2008 |
| WO | WO-2008/112927 A2 | 9/2008 |
| WO | WO-2008/112927 A3 | 9/2008 |
| WO | WO-2010/097716 A1 | 9/2010 |
| WO | WO-2011/055250 A2 | 5/2011 |
| WO | WO-2011/055250 A3 | 5/2011 |
| WO | WO-2011/101776 A1 | 8/2011 |
| WO | WO-2012/053910 | 4/2012 |
| WO | WO-2012/059768 | 5/2012 |
| WO | WO-2012/076614 | 6/2012 |
| WO | WO-2012/146991 A1 | 11/2012 |
| WO | WO-2013/096695 A2 | 6/2013 |
| WO | WO-2013/096695 A3 | 6/2013 |
| WO | WO-2014/110181 A1 | 7/2014 |
| WO | WO-2014/127044 A1 | 8/2014 |
| WO | WO-2015/031848 A2 | 3/2015 |
| WO | WO-2015/031848 A3 | 3/2015 |

(56) References Cited

FOREIGN PATENT DOCUMENTS

| WO | WO-2015/031850 A1 | 3/2015 |
|----|-------------------|--------|
| WO | WO-2015/143384 A1 | 9/2015 |
| WO | WO-2016/064925 A1 | 4/2016 |

OTHER PUBLICATIONS

International Search Report and Written Opinion for PCT/US2014/016105, dated Apr. 30, 2014, 7 pages.
International Search Report and Written Opinion for PCT/US14/10746, dated Apr. 15, 2014, 8 pages.
International Search Report and Written Opinion for PCT/US2014/053567 dated Dec. 18, 2014, 15 pages.
International Search Report and Written Opinion for PCT/US14/53572, dated Dec. 24, 2014, 8 pages.
Medtronic Capnography brochure MIN 3012492-001/CAT 21300-001569.
Molloy et al., "Are carbon dioxide detectors useful in neonates?" Arch Dis Child Fetal Neonatal Ed (2006) 91:F295-F298.
International Search Report and Written Opinion for PCT/US14/53569, dated Feb. 17, 2015, 18 pages.
Supplementary European Search Report for EP 12860711.6, dated Feb. 26, 2016, 6 pages.
Bartlett, R.G. et al. (1957). "Maximum breathing capacity with various expiratory and inspiratory resistances (single and combined) at various breathing rates," *J. Appl. Physiol.* 11(1):79-83.
Extended European Search Report dated Sep. 30, 2016, for European Patent Application No. 14 751 436.8, filed on Feb. 12, 2014, 8 pages.
International Search Report dated Apr. 30, 2014, for PCT Application No. PCT/US2014/016105, filed on Feb. 12, 2014, 2 pages.
International Search Report dated Jul. 2, 2015, for PCT Application No. PCT/US2015/021852, filed on Mar. 20, 2015, 2 pages.
International Search Report dated Feb. 9, 2016, for PCT Application No. PCT/US2015/056527, filed on Oct. 20, 2015, 4 pages.
Jaffe, M.B. (2002). "Mainstream of sidestream capnography?" Medical device depot Inc., White paper, 14 total pages.
Non-Final Office Action dated Dec. 18, 2015, for U.S. Appl. No. 14/150,625, filed Jan. 8, 2014, 13 pages.
Non-Final Office Action dated Oct. 21, 2016, for U.S. Appl. No. 14/473,888, filed Aug. 29, 2014, 22 pages.
Non-Final Office Action dated Nov. 10, 2016, for U.S. Appl. No. 14/179,381, filed Feb. 12, 2014, 12 pages.
Written Opinion of the International Searching Authority dated May 13, 2013, for PCT Application No. PCT/US2012/071085, filed on Dec. 20, 2012, 6 pages.
Written Opinion of the International Searching Authority dated Apr. 15, 2014, for PCT Application No. PCT/US2014/010746, filed on Jan. 8, 2014, 6 pages.
Written Opinion of the International Searching Authority dated Apr. 30, 2014, for PCT Application No. PCT/US2014/016105, filed on Feb. 12, 2014, 5 pages.
Written Opinion of the International Searching Authority dated Feb. 17, 2015, for PCT Application No. PCT/US2014/053569, filed on Aug. 29, 2014, 6 pages.
Written Opinion of the International Searching Authority dated Dec. 18, 2014, for PCT Application No. PCT/US2014/053567, filed on Aug. 29, 2014, 5 pages.
Written Opinion of the International Searching Authority dated Dec. 24, 2014, for PCT Application No. PCT/US2014/053572, filed on Aug. 29, 2014, 5 pages.
Written Opinion of the International Searching Authority dated Jul. 2, 2015, for PCT Application No. PCT/US2015/021852, filed on Mar. 20, 2015, 8 pages.
Written Opinion of the International Searching Authority dated Feb. 9, 2016, for PCT Application No. PCT/US2015/056527, filed on Oct. 20, 2015, 6 pages.
Extended European Search Report dated Jun. 8, 2016, for European Patent Application No. 14 737 690.9, filed on Jan. 8, 2014, 9 pages.
Extended European Search Report dated Mar. 16, 2017, for European Patent Application No. 14 839 697.1, filed on Aug. 29, 2014, 9 pages.
Extended European Search Report dated Jul. 12, 2017, for European Patent Application No. 14 838 958.8, filed on Aug. 29, 2014, 11 pages.
Final Office Action dated Mar. 21, 2017, for U.S. Appl. No. 14/150,625, filed Jan. 8, 2014, 14 pages.
Final Office Action dated Jun. 7, 2017, for U.S. Appl. No. 14/473,888, filed Aug. 29, 2014, 16 pages.
Final Office Action dated Aug. 16, 2017, for U.S. Appl. No. 14/179,381, filed Feb. 12, 2014, 11 pages.
Non-Final Office Action dated Mar. 23, 2017, for U.S. Appl. No. 14/664,728, filed Mar. 20, 2015, 18 pages.
Non-Final Office Action dated Apr. 20, 2017, for U.S. Appl. No. 14/473,878, filed Aug. 29, 2014, 10 pages.
Partial Supplementary European Search Report dated Apr. 7, 2017, for European Patent Application No. 14 838 958.8, filed on Aug. 29, 2014, 7 pages.
Coburn, R.F. et al. (1966). "Endogenous Carbon Monoxide Production in Patients with Hemolytic Anemia," Journal of Clinical Investigation 45:460-468.
Ebola Virus Infection (2017). Doctor-clinic.org, 2 total pages.
Extended European Search Report dated Oct. 16, 2017, for European Patent Application No. 15 764 503.7, filed on Mar. 20, 2015, 8 pages.
Final Office Action dated Oct. 19, 2017, for U.S. Appl. No. 14/664,728, filed Mar. 20, 2015, 18 pages.
Final Office Action dated Nov. 20, 2017, for U.S. Appl. No. 14/473,878, filed Aug. 29, 2014, 11 pages.
Non-Final Office Action dated Dec. 15, 2017, for U.S. Appl. No. 14/918,484, filed Oct. 20, 2015, 15 pages.
Non-Final Office Action dated Jan. 8, 2018, for U.S. Appl. No. 14/473,888, filed Aug. 29, 2014, 16 pages.
Non-Final Office Action dated Jan. 9, 2018, for U.S. Appl. No. 14/150,625, filed Jan. 8, 2014, 8 pages.

* cited by examiner

930

940

950

960

1120

1130

1140

1150

1220

1300

1310

1320

1330

1340

1350

1400

1420

| Linear Breath Rate Correction Factor Equations | |
|---|---|
| Breath Rate (bpm) | Equations |
| 10 - 30 | y = -M1x + b1 |
| 31 - 40 | y = -M2x + b2 |
| 41 - 60 | y = -M3x + b3 |
| Polynomial Breath Rate Correction Factor Equations | |
| Breath Rate (bpm) | Equation |
| 10 - 60 | y = -Ax² + Bx + C |
| y = ETCO; x = Breath Rate; M = slope; b = y intercept (or offset); A,B&C = polynomial equation constants. | |

1620

1640

COLLECTION AND ANALYSIS OF A VOLUME OF EXHALED GAS WITH COMPENSATION FOR THE FREQUENCY OF A BREATHING PARAMETER

CROSS-REFERENCE TO RELATED APPLICATIONS

This application claims the benefit of U.S. Provisional Application No. 61/578,811, filed Dec. 21, 2011, the disclosure of which is incorporated herein in its entirety.

FIELD OF THE INVENTION

Described here are devices and methods for the analysis of breath exhalant for diagnostic purposes. More specifically, devices and methods for sampling and analysis of gas from a person's breath for correlation to and diagnosis of an underlying physiologic condition are described.

BACKGROUND

There are two general techniques employed for obtaining a person's breath for gas analysis. In a first technique a person can cooperatively breathe into an instrument, which receives the gas for analysis. In a second technique an instrument can obtain a gas sample from the person's airway independent of the person's cooperation. In either technique, achieving a precise collection and precise analysis of a gas from a specific portion of the breathing cycle can be challenging, given the often random and erratic nature of a breathing pattern. For example, reliably measuring breath CO at exactly the end-tidal portion of exhalation, with high levels of accuracy and precision (for example <0.5 ppm accuracy), has proven difficult. Typically, a measurement of breath $CO_2$ is used to determine the end-tidal portion of the breath, and gas from that portion of the breath can be sampled and analyzed accordingly. Using an end-tidal $CO_2$ signal is a convenient approach in that the technology is well known, and provides an instantaneous measurement of the breath waveform. However, in order to obtain accuracy and precision in the remainder of the overall system, the instrumentation considers only some of the possible external factors that may be useful.

Typically, a constant flow rate is employed for withdrawing the gas from the person, for a fixed collection time, and placing the drawn sample in a fixed volume sample compartment. When using this approach, there may be breath pattern related inaccuracies. For example, some of the sample compartment may have non-end-tidal gas in it, or only a fraction of the end-tidal portion of the breath might get sampled and stored in the sample compartment for analysis. While the repeatability at a certain breath rate is very good, the accuracy may vary as the breath rate varies, because of the pneumatics and timing of the system.

Therefore, it may be beneficial to improve on the accuracy of known systems in a way that is equally accurate across a range of breath patterns and breath rates. To this end, various approaches and algorithms have been conceived and described herein.

BRIEF SUMMARY

Described herein are breath gas analyzers that achieve an accurate compositional analysis of a breath-borne gas from a specific portion of a breath. The system can accommodate a wide range of breathing patterns and rates without losing accuracy. The system can assure that enough volume of gas is obtained for the analysis to be sufficiently accurate, and that the gas obtained is from the desired portion of the breath, and is representative of the entire desired portion of the breath. In some variations, these advantages are achieved by modulating the gas sampling flow rate depending on the breath pattern, and/or by obtaining gas samples from the desired portion of the breath for multiple breaths until a threshold volume of gas is obtained for analysis, and/or by applying a correction factor to the computed result to compensate for heterogeneity of the sampled gas. In addition to these methods for obtaining target volumes of gas, some variations may identify the desired portion of the breath in order to accurately sample the correct portion of the breath and/or tune the system to always collect for analysis a substantially homogenously end-tidal sample regardless of breathing pattern.

To achieve the above features, variations of a breath analyzer or method for analyzing breath may include one or more of the following benefits: identification of different sub-portions of an expiratory phase; accurate sample collection from a desired sub-portion of the expiratory phase; assured collection of a predetermined quantity of gas for analysis by a gas composition analyzer; reliability and repeatable for a wide variety of breathing patterns that are expected to be encountered.

In one variation, a method for breath analysis comprises measuring a time-related parameter of a person's breathing pattern, collecting gas from a target portion of at least one of the person's breaths into a sample compartment having a target volume, adjusting the gas collection based on the time-based-parameter, and analyzing the collected gas to determine a compositional parameter of the gas. In further variations, adjusting the gas collection can include at least one selected from the group consisting of: (1) adjusting the gas collection speed, (2) adjusting the number of breaths the gas is collected from, and (3) adjusting for the homogeneity of the collected gas with a correction factor. In yet further variations, the time-based-parameter comprises at least one parameter selected from the group consisting of: (1) breath rate, (2) end-tidal time period, (3) expiratory time period, (4) inspiratory time period, (5) breath period. In further variations, the target portion of the breath comprises the end-tidal portion and the compositional parameter comprises carbon monoxide. In further variations, the target portion of the breath comprises at least one phase selected from the group consisting of: (1) an expiratory phase; (2) an end-tidal phase; (3) a beginning portion of exhalation; (4) a middle portion of exhalation; (5) a last portion of exhalation; (6) a post-expiratory period; and (7) an inspiratory pause. In further variations, measuring a time-based parameter comprises at least one technique selected from the group consisting of: (1) capnometry, (2) monitoring airway pressure, (3) monitoring airway temperature, (4) monitoring airway flow, (5) plethysmography, (6) monitoring sound, and (7) monitoring exhaled oxygen. In yet further variations, the time-based-parameter is differentiated to determine a time period of a target breath portion. Further variations may include defining a start time and an end time for collecting the gas, wherein defining a start time and an end time comprises comparing the measured breath parameter against at least one selected from the group consisting of: (1) a threshold amplitude of the measured breath parameter; (2) a threshold time period of the measured breath parameter, (3) a peak value of the measured breath parameter, (4) a substantially zero value of the measured breath parameter, (5) a negative value of the measured breath parameter, (6) a change in slope of the measured breath parameter, and (7) a change in sign of the measured breath parameter. Other variations may include defining a start time and an end time for collecting the gas wherein defining a start time and an end time comprises calculating a rate of change of the measured breath parameter and comparing it to at least one selected from the group consisting of: (1) a threshold value of the rate of change; (2) a zero value of the rate of change; (3) a first rate of change against a second rate of change; (4) a negative slope approaching zero; (5) a positive slope approaching zero; (6) a peak positive value of the rate of change; (7) a peak negative value of the rate of change; (8) an increasing rate of change; (9) a decreasing rate of change; and (10) a sign change of the rate of change. In further variations, collecting the gas further comprises applying a sampling cannula in communication with the sample compartment to the person's airway, and applying a vacuum to the sampling cannula. Further variations may include isolating the sample compartment with an inlet valve, and opening the inlet valve to begin collecting the gas from the target breath portion and closing the inlet valve to finish collecting the gas from the target breath portion. In further variations, the gas collected in the sample compartment comprises at least a portion of a breath from which the time-based breath parameter is measured. In further variations, the gas collected in the sample compartment comprises at least a portion of a breath that is not a breath from which the time-based breath parameter is measured.

In another variation, a method for breath analysis comprises identifying a time period of a portion of a breath, collecting a gas sample from the portion in a sample compartment having a target volume, wherein the gas sample is drawn into the compartment using a flow mechanism, and wherein a flow rate of the mechanism is based on the identified time period, and analyzing the collected gas sample for compositional analysis.

In another variation, a method for breath analysis comprises measuring an end-tidal time period of a person's breathing pattern with a breath sensor, collecting gas from the end-tidal period of at least one of the person's breaths into a sample compartment having a target volume with a flow mechanism, wherein the collection flow rate of the flow mechanism is adjusted based on the measured end-tidal time period and selected to substantially fill the target volume with gas from the end-tidal period, and analyzing the collected gas to determine a compositional parameter of the gas.

In another variation, a method for breath analysis comprises the steps (a) identifying a time period of a portion of a breath, (b) collecting a gas sample from the portion in a sample compartment having a target volume, wherein the gas sample is drawn into the compartment using a flow mechanism, (c) wherein (a) and (b) are repeated for a number of times, wherein the number of times is determined at least in part by the identified time period, and (d) analyzing the collected gas sample for compositional analysis.

In another variation, a method for breath analysis comprises (a) measuring an end-tidal time period of a person's breathing pattern with a breath sensor, (b) collecting gas from the end-tidal period of the person's breath into a sample compartment having a target volume using a flow mechanism, (c) wherein (a) and (b) are repeated until the compartment is substantially filled with gas from end-tidal periods, and (d) analyzing the collected gas to determine a compositional parameter of the gas. In another variation, the method includes tuning the breath collection system to always collect a substantially homogenously end-tidal sample, regardless of breathing pattern Also described herein are various breath gas analyzers. In one variation, an apparatus for analyzing gas in a target portion of a person's breath cycle comprises a sample compartment of a target volume, a pneumatic system operable to collect gas from a person's breath and deliver the gas to the sample compartment, a breath sensor operable to measure a time-based-parameter of the target portion of the person's breath, a control system operable to adjust the pneumatic system based on the time-based-breath parameter, and an analyzer for analyzing the gas composition. In further variations, a gas flow system adjustment is provided that comprises at least one adjustment selected from the group consisting of: (1) an adjustable speed flow generator; (2) a processor configured to execute an algorithm that varies the number of breaths gas is collected from, and (3) a processor configured to execute an algorithm to adjust for the homogeneity of the collected gas with a correction factor. In further variations, the time-based-component comprises at least one component selected from the group consisting of: (1) a breath rate, (2) an end-tidal time period, (3) an expiratory time period, (4) an inspiratory time period, and (5) a breath period. In further variations, the target portion of the breath comprises the end-tidal portion and the gas analyzer comprises a carbon monoxide analyzer. In further variations, the target portion of the breath comprises at least one portion selected from the group consisting of: (1) an expiratory phase; (2) an end-tidal phase; (3) a beginning portion of exhalation; (4) a middle portion of exhalation; (5) a last portion of exhalation; (6) a post expiratory phase; and (7) an inspiratory pause. In further variations, the breath sensor comprises at least one selected from the group consisting of: (1) a capnometer, (2) an airway pressure transducer, (3) an airway temperature sensor, (4) an airway flow sensor, (5) a plethysmograph, (6) a microphone, (7) an oxygen sensor, and (8) an ultrasonic sensor. In further variations, the apparatus further comprises (1) a differentiator adapted to differentiate the signal from the breath sensor and (2) a processor, wherein the processor executes an algorithm to correlate the differentiated signal to the target portion of the breath cycle. In further variations, the apparatus further comprises a processor, wherein the processor executes an algorithm to determine the start time and end time for collecting the gas, wherein the algorithm comprises a comparison of the measured breath parameter against at least one selected from the group consisting of: (1) a threshold value, (2) a threshold time period, (3) a peak value, (4) a substantially zero value, (5) a negative value, (6) a change in slope, and (7) a change in sign. In further variations, the apparatus comprises a differentiator to determine a rate-of-change of the measured breath parameter, and a processor to execute an algorithm, wherein the algorithm comprises a comparison of the rate of change with at least one selected from the group consisting of: (1) a threshold value; (2) a zero value; (3) a first rate of change against a second rate of change; (4) a negative slope approaching zero; (5) a positive slope approaching zero; (6) a peak positive value; (7) a peak negative value; (8) an increasing rate of change; (9) a decreasing rate of change; and (10) a sign change of the rate of change. In further variations, the apparatus further comprises a sampling cannula attachable at a first end to the gas analysis apparatus and engageable at a second end to the person's airway; and a flow generator adapted to draw gas from the person's airway through the sampling cannula to the sample compartment. In further variations, the apparatus comprises a valve system arranged to isolate the sample compartment, wherein the control system controls the valve system to permit gas from the target breath portion to enter the sample compartment. In further variations, the control system is further adapted to deliver gas to the sample compartment from the measured breath. In further variations, the control system is further adapted to deliver gas to the sample compartment from a breath after the measured breath.

In another variation, a breath gas analyzer for analyzing gas in a target portion of a person's breath comprises a breath sensor for identifying the target portion of the breath cycle, a processor for determining the time period of the target portion, wherein the time period is determined at least in part from the identified portion, a gas collection compartment of a target volume, a pneumatic system for delivering a gas sample from the target portion of the breath to the gas collection compartment, a control system for adjusting the gas delivery rate of the pneumatic system based on the determined time period, and a gas analyzer for analyzing the composition of the gas.

In another variation, a breath gas analyzer for analyzing gas in the end-tidal portion of a person's breath comprises a breath sensor for identifying the end-tidal period of the breath cycle, a processor for determining the time period of the end-tidal period, wherein the time period is determined at least in part from the identified portion, a gas collection compartment of a target volume, a vacuum source for drawing a gas sample from the end-tidal period of the breath to the gas collection compartment, a control system for adjusting the flow rate of the vacuum source based on the determined end-tidal time period to substantially fill the compartment with end-tidal gas, and a gas analyzer for analyzing the composition of the gas.

In another variation, a breath gas analyzer for analyzing gas in a target portion of a person's breath, comprises a breath sensor for identifying the target portion of the breath cycle, a processor for determining the time period of the target portion, wherein the time period is determined at least in part from the identified portion, a gas collection compartment of a target volume, a pneumatic system for delivering a gas sample from the target portion of the breath to the gas collection compartment, a control system and algorithm for controlling the pneumatic system to deliver gas until the compartment is substantially filled with gas from the target breath portion, and a gas analyzer for analyzing the composition of the gas.

In another variation, a breath gas analyzer for analyzing gas in a target portion of a person's breath comprises a breath sensor for identifying the target portion of the breath cycle, a processor for determining the time period of the target portion, wherein the time period is determined at least in part from the identified portion, a gas collection compartment of a target volume, a pneumatic system for capturing a gas sample from the target portion of the breath into the gas collection compartment, a processor for executing an algorithm for applying a correction factor to the captured gas sample, wherein the correction factor is based on the determined time period of the target breath portion to correct for the non-homogeneity of the captured gas, and a gas analyzer for analyzing the composition of the gas.

In another variation, a method for breath analysis comprises (a) identifying a time period of an end-tidal portion of a breath, (b) collecting the end-tidal portion in a sample tube having a sample volume, wherein a time of collection is based on the identified time period, (c) repeating steps (a) and (b) until the sample volume is filled with a plurality of end-tidal portions from a respective plurality of breaths, and (d) analyzing the collected plurality of end-tidal portions to determine the concentration of a gas.

In another variation, a breath gas analyzer comprises a system operable to measure at least one characteristic of a patient's breath, a processor operable to determine a starting and an ending point of an end-tidal portion of the breath, wherein the determination is based upon the at least one characteristic, a sample tube comprising a proximal end, a distal end, a first valve coupled to the proximal end, a second valve coupled to the distal end, and a sample volume, wherein the sample volume is configured to store a plurality of end-tidal breath portions from a respective plurality of breaths, and a sensor for analyzing the concentration of a gas in the stored plurality of end-tidal breaths.

In another variation, a method of collecting an end-tidal portion of a patient's breath comprises identifying a starting point of the end-tidal portion, opening a container configured to collect the end-tidal portion, wherein the container is opened to correlate to the identified starting point of the end-tidal portion, identifying an ending point of the end-tidal portion, and closing the container, wherein the container is closed to correlate to the identified ending point of the end-tidal portion.

In another variation, a gas measurement correction database for determining a gas concentration at an inlet of an apparatus is populated by a method that may include measuring a plurality of gas concentrations in the apparatus for a respective plurality of known gas concentrations at the inlet (wherein the gas concentrations are measured at a plurality of breath rates), deriving a first plurality of polynomial equations (wherein each of the first plurality of polynomial equations fits the measured gas concentrations of a respective one of the plurality of breath rates and wherein each of the first plurality of polynomial equations comprises a coefficient at each order of the equation), deriving a second plurality of polynomial equations (wherein each of the second plurality of polynomial equations fits the coefficients of a respective order of the first plurality of polynomial equations wherein each of the second plurality of polynomial equations comprises a coefficient at each order of the equation), and recording each of the coefficients of the second plurality of polynomial equations in the database. The first plurality of polynomial equations may comprise a plurality of linear equations. The plurality of breath rates may be at least five in number. The plurality of breath rates may include breath rates of 10 breaths per minute, 20 breaths per minute, 30 breaths per minute, 40 breaths per minute, and 50 breaths per minute. The second plurality of polynomial equations may comprise a plurality of quadratic equations. The coefficients of the second plurality of polynomial equations may comprise a first plurality of coefficients and a second plurality of coefficients, wherein the first plurality of coefficients correspond to breath rates at or below a predetermined breath rate and the second plurality of coefficients correspond to breath rates at or above the predetermined breath rate. The predetermined breath rate may be 30 bpm. The second plurality of polynomial equations may comprise a first plurality of quadratic equations and a second plurality of quadratic equations, wherein each of the first plurality of quadratic equations fits the first plurality of coefficients at each order, and wherein each of the second plurality of quadratic equations fits the second plurality of coefficients at each order. The plurality of known gas concentrations at the inlet may comprise three in number. The plurality of known gas concentrations at the inlet may comprise at least one selected from each of the following: a region of relatively low breath rate, a region of relatively high breath rate, and a region of intermediate breath rate.

In another variation, a method for determining a gas concentration of a patient's breath at an inlet of an apparatus may comprises determining a breath rate of the patient, measuring a gas concentration in the apparatus, accessing a database to obtain a first plurality of coefficients corresponding to the patient's breath rate, deriving a first plurality of polynomial equations based on the first plurality of coefficients, deriving a second plurality of coefficients by inputting the breath rate into each of the first plurality of polynomial equations, deriving a compensation equation using the second plurality of coefficients, and determining the gas concentration at the inlet by inputting the measured gas concentration into the compensation equation. Each of the first plurality of polynomial equations may be a quadratic equation and the first plurality of coefficients may be three in number. The compensation equation may be linear and the second plurality of coefficients may be two in number. The database may include a first subset of coefficients and a second subset of coefficients, wherein the first subset of coefficients correspond to breath rates at or below a predetermined breath rate and the second subset of coefficients correspond to breath rates at or above the predetermined breath rate. The predetermined breath rate may be 30 bpm.

In another variation, an apparatus for analyzing a gas concentration of a patient's breath may comprise a gas analyzer that measures a gas concentration in the apparatus, an inlet that receives the patient's breath, a breath speed analyzer that determines a breathing parameter frequency of the patient's breath, a database comprising a plurality of coefficients corresponding to a plurality of breathing parameter frequencies, and a processor containing a non-transitory computer readable medium containing executable instructions that when executed perform a method of determining the gas concentration of the patient's breath at the inlet of the apparatus, wherein the method includes accessing the database to obtain a first plurality of coefficients based on the patient's breathing parameter frequency, deriving a first plurality of polynomial equations based on the first plurality of coefficients, deriving a second plurality of coefficients by inputting the breathing parameter frequency into each of the first plurality of polynomial equations, deriving a compensation equation using the second plurality of coefficients, and determining the inlet gas concentration by inputting the measured gas concentration into the compensation equation. The first plurality of polynomial equations may be a quadratic equation and the first plurality of coefficients may be three in number. The compensation equation may be linear and the second plurality of coefficients may be two in number. The database may comprise a first subset of coefficients and a second subset of coefficients, wherein the first subset of coefficients correspond to breathing parameter frequencies at or below a predetermined breathing parameter frequency and the second subset of coefficients correspond to breathing parameter frequencies at or above the predetermined breathing parameter frequency. The predetermined breathing parameter frequency may be 30 bpm.

In another variation, a method for determining a gas concentration of a patient's breath at an inlet of an apparatus includes determining a breathing parameter frequency of the patient, measuring a gas concentration in the apparatus, accessing a database to obtain a plurality of coefficients based on whether the patient's breathing parameter frequency is at, above, or below a predetermined breathing parameter frequency, wherein the database comprises a first subset of coefficients and a second subset of coefficients, wherein the first subset of coefficients correspond to breathing parameter frequencies at or below the predetermined breathing parameter frequency and the second subset of coefficients correspond to breathing parameter frequencies at or above the predetermined breathing parameter frequency, deriving a compensation equation using the plurality of coefficients, and determining the gas concentration at the inlet by inputting the measured gas concentration into the compensation equation. The predetermined breathing parameter frequency may be 30 bpm.

In another variation, an apparatus for analyzing a gas concentration of a patient's breath may comprise a gas analyzer that measures a gas concentration in the apparatus, an inlet that receives the patient's breath, a breath speed analyzer that determines a breathing parameter frequency of the patient's breath, a database comprising a plurality of coefficients corresponding to a plurality of breathing parameter frequencies, wherein the database comprises a first subset of coefficients and a second subset of coefficients, wherein the first subset of coefficients correspond to breathing parameter frequencies at or below a predetermined breathing parameter frequency and the second subset of coefficients correspond to breathing parameter frequencies at or above the predetermined breathing parameter frequency, and a processor containing a non-transitory computer readable medium containing executable instructions that when executed perform a method of determining the gas concentration of the patient's breath at the inlet of the apparatus, the method including accessing the database to obtain a plurality of coefficients based on whether the patient's breathing parameter frequency is at, above, or below the predetermined breathing parameter frequency, deriving a compensation equation based on the plurality of coefficients, and determining the inlet gas concentration by inputting the measured gas concentration into the compensation equation. The predetermined breathing parameter frequency may be 30 bpm.

In another variation, a method for determining a gas concentration of a patient's breath at an inlet of an apparatus may comprise determining a breathing parameter frequency of the patient, measuring a gas concentration in the apparatus, accessing a database to obtain a plurality of coefficients corresponding to the patient's breathing parameter frequency, deriving a compensation equation using the plurality of coefficients, and determining the gas concentration at the inlet by inputting the measured gas concentration into the compensation equation. The compensation equation may be a polynomial equation. The compensation equation may be linear. The database may comprise a first subset of coefficients and a second subset of coefficients, wherein the first subset of coefficients correspond to breathing parameter frequencies at or below a predetermined breathing parameter frequency and the second subset of coefficients correspond to breathing parameter frequencies at or above the predetermined breathing parameter frequency. The predetermined breathing parameter frequency may be 30 bpm.

In another variation, an apparatus for analyzing a gas concentration of a patient's breath comprises a gas analyzer that measures a gas concentration in the apparatus, an inlet that receives the patient's breath, a breath speed analyzer that determines a breathing parameter frequency of the patient's breath, a database comprising a plurality of coefficients corresponding to a plurality of breathing parameter frequencies, and a processor containing a non-transitory computer readable medium containing executable instructions that when executed perform a method of determining the gas concentration of the patient's breath at the inlet of the apparatus, the method comprising accessing the database to obtain a plurality of coefficients based on the patient's breathing parameter frequency, deriving a compensation equation using the plurality of coefficients, and determining the inlet gas concentration by inputting the measured gas concentration into the compensation equation. The compensation equation may be a polynomial equation. The polynomial equation may be a linear equation. The database may comprise a first subset of coefficients and a second subset of coefficients, wherein the first subset of coefficients correspond to breathing parameter frequencies at or below a predetermined breathing parameter frequency and the second subset of coefficients correspond to breathing parameter frequencies at or above the predetermined breathing parameter frequency. The predetermined breathing parameter frequency may be 30 bpm.

In another variation, an apparatus for collecting gas from a patient's breath comprises a sample volume, a flow generator comprising a sampling flow rate (wherein the flow generator may completely, or nearly completely, fill the sample volume with an end-tidal portion of the patient's breath when the patient's breath has a determined breathing parameter frequency), and a processor configured to discard a gas collected from the patient's if a breathing parameter frequency of the patient exceeds the predetermined breathing parameter frequency. The flow generator may be a pump. The end-tidal period of the patient's breath may be assumed to be a fraction such as one quarter of a breath period of the patient, wherein the breath period comprises one inspiratory and expiratory cycle of the patient's breath.

In another variations, an apparatus for analyzing a gas concentration of a sample of a patient's breath may comprise a sample compartment with an inlet that receives the patient's breath, a breath speed analyzer that determines the speed of a portion of the patient's breath, a gas analyzer that determines a gas concentration of the gas in the sample compartment, and a processor comprising an algorithm that determines a corrected gas concentration based on the speed of a portion of the patient's breath, wherein the corrected gas concentration is determined independently of patient cooperation.

In another variation, an apparatus for analyzing a gas concentration of a sample of a patient's breath may comprise a sample compartment with an inlet that receives the patient's breath, a breath speed analyzer that determines the speed of a portion of the patient's breath, a gas analyzer that determines a gas concentration of the gas in the sample compartment, and a processor comprising an algorithm, wherein the algorithm determines a degree of non-homogeneity of the breath sample in the sample compartment based on the speed of a portion of the patient's breath, wherein the algorithm determines a corrected gas concentration based on the degree of non-homogeneity, and wherein the corrected gas concentration is determined independently of patient cooperation.

In another variation, an apparatus for analyzing a gas concentration of a sample of a patient's breath may comprise a breathing parameter frequency measuring sensor, an algorithm comprising a defined maximum breathing parameter frequency, a sample compartment with a volume and with an inlet that receives the patient's breath, a gas analyzer that determines a gas concentration of the gas in the sample compartment, and a sampling flow rate control unit that delivers the sample from the patient into the sample compartment at a desired rate, wherein the sample compartment volume and the desired rate are determined based on the defined maximum breathing parameter frequency.

BRIEF DESCRIPTION OF THE DRAWINGS

FIG. 3A describes the CO level in the breath for different phases of the breathing cycle. FIG. 3B describes the $CO_2$ level in the breath for different phases of the breathing cycle and threshold values to identify the end-tidal period. FIG. 3C describes the proximal airway breathing pressure for different phases of the breathing cycle and threshold values to identify the end-tidal period.

FIGS. 8-9G describe one variation of a breath analysis device using a breath rate correction factor to correct for breath rate related variations in the heterogeneity of the sampled gas, when using a fixed sampling flow rate with a fixed sampling time and a fixed sample collection tube volume. FIG. 8 is a graph of a capnometry signal for a sequence of breaths. FIG. 9G describes the system of FIGS. 9C and 9D in which a breath is captured from a relatively slow breath rate.

FIG. 10A is a schematic flow diagram describing the multiple breath sampling technique. FIG. 10B illustrates a graph of the number of breaths that may be necessary to fill an exemplary sample volume for a series of breath rates.

FIG. 11A graphically describes the capnometry signal and sample capture valve position, of an exemplary breath rate modulated multiple breath sampling protocol. FIGS. 11B-11F describe the pneumatic system described in FIG. 5A or 5B for an exemplary end-tidal gas capture. FIG. 11B describes the pneumatic gas capture system of FIG. 5A or 5B with end-tidal gas from the first breath being captured. FIG. 11C describes the pneumatic gas capture system of FIG. 5A or 5B with the second breath being staged for capturing. FIG. 11D describes the pneumatic gas capture system of FIG. 5A or 5B with end-tidal gas from the second breath being captured. FIG. 11E describes the pneumatic gas capture system of FIG. 5A or 5B with the third breath being staged for capturing. FIG. 11F describes the pneumatic gas capture systems of FIG. 5A or 5B with end-tidal gas from the third breath being captured.

FIG. 12A describes a schematic flow diagram of the sequence of operation of a breath-rate-modulated variable sampling flow rate technique. FIG. 12B illustrates a graph of a sampling flow rate versus corresponding end-tidal time periods for an example sample volume.

FIG. 13A graphically describes a breath capnometry signal for a relatively fast breath rate. FIG. 13B graphically describes a breath capnometry signal for a relatively slow breath rate. FIG. 13C describes a pneumatic diagram of the gas collection system for the breath shown in FIG. 13A for an exemplary end-tidal gas capture, adjusted to a relatively fast sampling flow rate. FIG. 13D describes a pneumatic diagram of the gas collection system for the breath shown in FIG. 13B, adjusted to a relatively slow sampling flow rate. FIG. 13E describes using a capnometry signal to determine an average end-tidal time of previous breaths and a respective adjustment of the sampling flow rate to collect the targeted volume of end-tidal gas from a single subsequent breath. FIG. 13F describes using an airway pressure signal to determine a projected end-tidal time from a measurement of a pre-end-tidal period, and a respective adjustment of the sampling flow rate to collect the targeted volume of end-tidal gas from the breath.

FIG. 14A is a graph illustrating ETCO ppm as a function of breath rate. FIG. 14B provides at table with some exemplary breath rate correction factor equations.

DETAILED DESCRIPTION

Described here are devices and methods for capturing and analyzing an exhaled breath. In some variations, one or more breathing parameters are measured to identify the different constituent portions of a breath and the respective time periods, and a pneumatic system is used for capturing the portion of exhaled breath in a sampling tube using an identified time period. In some variations, one or more valves and/or flow control mechanisms—such as a vacuum pump, for example—are used to regulate the flow rate of gas drawn into the sampling tube. In some variations, the captured portion of breath is analyzed for indications of a patient's physiological state.

A portion of a breath may include an end-tidal portion, a beginning portion, a middle portion, and an end portion of an exhaled breath. Measured breathing parameters may include one or more of carbon dioxide, oxygen, airway pressure, airway temperature, breath flow rate, and breath pressure. Identifying the time period of a portion of a breath may include identifying approximately the start and termination of that time period.

In some variations of a multiple breath end-tidal sample collection algorithm, the number of samples collected varies with the breath rate, in order to fill a fixed sample collection volume with the complete end-tidal portion of the breath(s). In some variations of a variable sampling vacuum rate algorithm, vacuum rate is modulated based on a breath rate, allowing the sample collected to be the entire end-tidal section of the breath.

The composition of exhaled gas may vary corresponding to different stages of the expiratory period. For example, gas sampled near the end of exhalation may be representative of gas that has most recently diffused out of the blood stream into the alveoli. In the example shown in FIG. 1, described below, the expiratory period is divided into two portions: pre-end-tidal and end-tidal. During the pre-end-tidal portion, gas from the conducting airways and from the distal portions of the lung are expelled, and during the end-tidal portion, gas that has freshly diffused into the alveolar volume is expelled. A diagnostic gas sample may be best taken from the end-tidal period, for example when attempting to diagnose a physiologic condition in the blood stream, such as hyperbilirubinemia or hemolysis. For explanatory purposes, exemplary variations for sampling end-tidal gas for end-tidal CO measurement are given below, however the principles apply to other diagnostic purposes.

Figure 1:
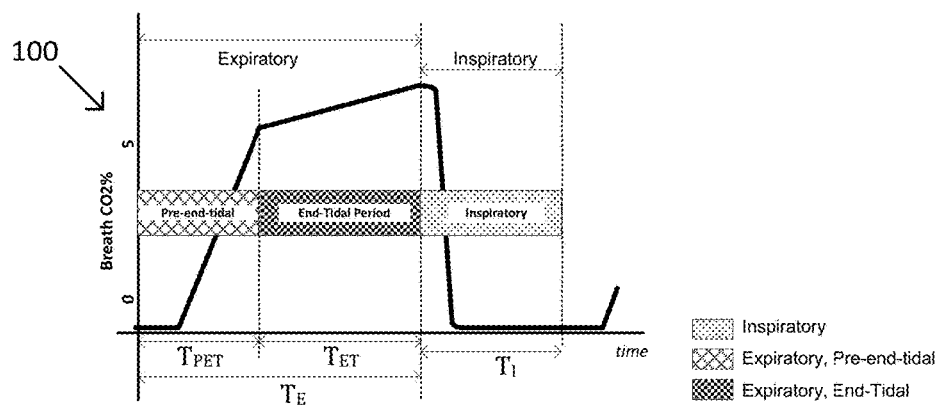
FIG. 1 graphically describes a typical breath waveform based on a carbon dioxide measurement taken on gas drawn from a breath.

FIG. 1 graphically describes a typical breathing pattern 100 from the perspective of a carbon dioxide ($CO_2$) signal measured in breath drawn from the person's airway, such as from their nose, as a function of time, with time on the horizontal axis, and $CO_2$ level on the vertical axis. During the expiratory phase $CO_2$ is expelled, hence the $CO_2$ level increases. During the inspiratory phase, ambient air occupies the nose, hence the measured $CO_2$ drops to essentially zero. There may be a variety of shapes to a breath $CO_2$ curve, based on the person's breathing pattern, their age, how they are breathing and any underlying acute or chronic medical conditions. Some curves may show the following sub-portions for the expiratory phase: (1) a beginning portion of low or no $CO_2$ because the gas may simply be gas from the proximal airway devoid of $CO_2$, (2) a middle portion showing $CO_2$ rapidly increasing from zero to the $CO_2$ level at the distal segments of the lungs, (3) an end-portion showing a plateauing or leveling off of the $CO_2$, representing the $CO_2$ coming from the alveoli for that exhaled breath, and (4) potentially a constant peak level at the very end of the expiratory period. However, there can be many other curves different from this classic curve. Peak CO2 levels may be 4-6% during the end-tidal period and close to or equal to zero during the inspiratory period.

In some variations, the level of $CO_2$ in an exhaled breath is used to determine the duration of a period of a breath. In further variations, a duration of a period of breath may be characterized by a start and a termination of that period. In some variations, a $CO_2$ level is used to determine a start or a termination of a period of a breath. In other variations, a first time derivative of a $CO_2$ level is used to determine a start or a termination of a period of a breath. In yet other variations, a second time derivative of a $CO_2$ level is used to determine a start or a termination of a period of a breath. In some variations, a combination of $CO_2$ levels and $CO_2$ level time derivatives may be used to determine a start or a termination of a period of a breath. In some variations, a start of an end-tidal period may be determined by a change in the first time derivative of a $CO_2$ level of the exhaled breath, such as a sudden decrease in the first time derivative of the $CO_2$ level. In some variations, a decrease in the first time derivate of the $CO_2$ level is more than a 10% decrease. In some variations, a decrease in the first time derivate of the $CO_2$ level is more than a 25% decrease. In some variations, the derivative will approach or become zero showing very little rate of change or a peak plateau, respectively. In other variations, the start of an end-tidal period may be determined by a large second time derivative of the $CO_2$ level. In some variations, a termination of an end-tidal period may be determined by a maximum $CO_2$ level, which may be detected or confirmed by a change in the sign of the first time derivative of the $CO_2$ level as the derivative becomes negative (associated with a drop of the CO2 level from its peak value). In further variations, a start of a beginning period may be determined by a sudden increase in the first time derivative of the $CO_2$ level. In other variations, the start of a beginning period may be determined by an increase in the $CO_2$ level from zero $CO_2$ level. In some variations, the increase in $CO_2$ level may be non-zero, such as near-zero or from a baseline. In some variations, a termination of a middle period may be determined by a change in the first time derivative of a $CO_2$ level of the exhaled breath, such as a sudden decrease in the first time derivative of the $CO_2$ level. In some variations, a $CO_2$ level, first time derivative thereof, second time derivative thereof, or a combination of the foregoing may be used to determine the start and termination of one or more periods.

Figure 2:
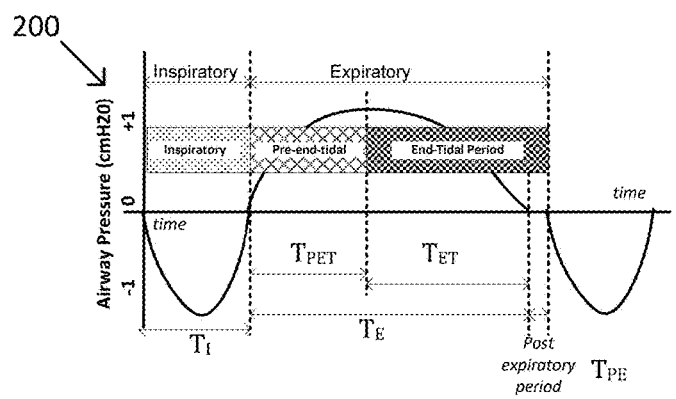
FIG. 2 graphically describes a typical breath waveform based on an airway pressure measurement taken at the proximal airway.

FIG. 2 graphically describes a typical breathing signal 200 from the perspective of measured airway pressure, showing a negative pressure during inspiratory phase and a positive pressure during expiratory phase. During at rest breathing, the peak expiratory pressure may correspond to the middle of the expiratory phase and the start of the end-tidal period. In FIGS. 1 and 2, TI, TE, TPET, TET, TPE represent inspiratory time, expiratory time, pre-end-tidal time, end-tidal time, and post expiratory time respectively. An inspiratory pause may also be present (not shown), in which lung muscle movement during inspiration is paused before the expiratory period begins. Peak inspiratory pressure may be −1 to −4 cwp during restful breathing, and up to −15 cwp during heavier breathing, and peak expiratory pressure may be +0.5 to +2.0 cwp during restful breathing and up to +10 cwp during heavier breathing when measured at the entrance to the nostrils. One of skill in the art will readily recognize that the cwps given here are exemplary and that other cwps may be present without deviating from the scope of this disclosure.

In some variations, airway pressure is used to determine a start or a termination of a period of a breath. In other variations, a first time derivative of an airway pressure is used to determine a start or a termination of a period of a breath. In yet other variations, a second time derivative of an airway pressure is used to determine a start or a termination of a period of a breath. In some variations, a combination of airway pressures and airway pressure time derivatives may be used to determine a start or a termination of a period of a breath. In some variations, a start of an end-tidal period is determined by maximum airway pressure, that is, by a zero first time derivative of the airway pressure. In some variations, a termination of an end-tidal period may be determined by zero airway pressure. In some variations, an airway pressure, first time derivative thereof, second time derivative thereof, or a combination of the foregoing may be used to determine the start and termination of one or more periods.

In some variations, the breath sensor monitors the person's breathing over time, and trends the breathing pattern by determining a continually updated value that is characteristic of the breathing pattern. For example, peak positive values of a breathing signal may be measured and updated for each breath. Peak values may be compared with previous peak values. Peak values may be averaged over a previous number of multiple breaths. Similarly, time-related aspects of the breaths may be trended, such as the expiratory time. Various breath-related events that are not normal breaths may be identified and exception algorithms may exist in order to not include these non-normal breath events inadvertently in deterministic steps. For example, the characteristic waveform of a sneeze, cough, stacked breath, or non-full breath may be defined in advance or based on monitoring of a particular patient, and when detected by the breathing sensor, excepted from the appropriate deterministic algorithms.

Figure 3A:
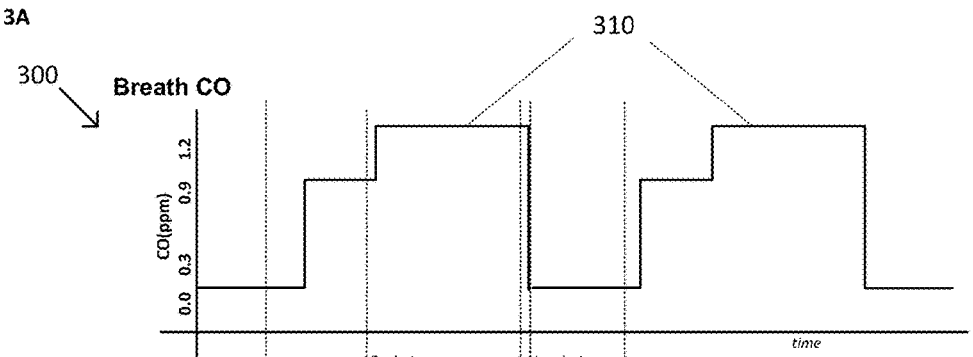
FIGS. 3A-3C graphically describe how breath CO may vary with the phase of the breath and one variation of using capnometry or airway pressure to identify the end-tidal period of the breath.
Figure 3B:
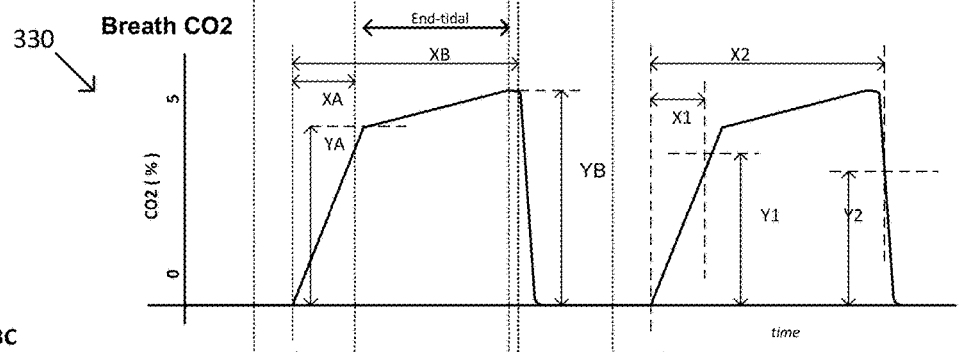
Figure 3C:
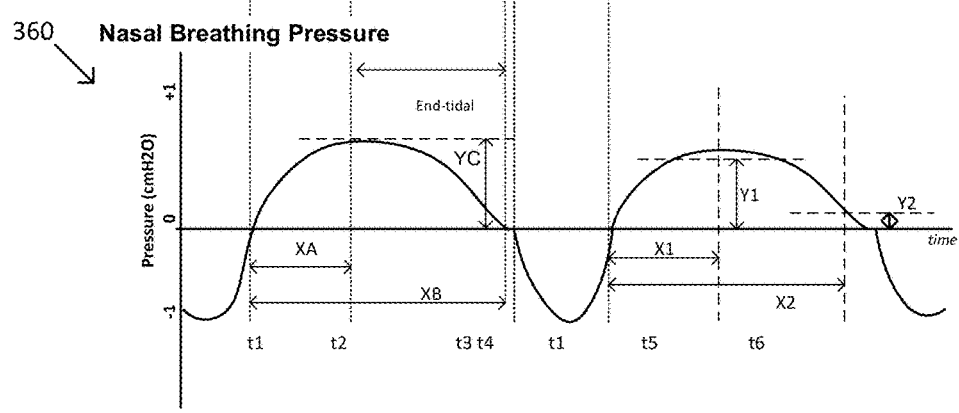

FIGS. 3A-3C describe in more detail one variation of using a breath signal to identify a portion of the breath cycle for capturing a desired sample for compositional analysis. In the example shown, a capnometry signal or an airway pressure signal is used to identify the end-tidal portion of the expiratory phase for measurement of end-tidal CO. In FIG. 3A, the breath CO level 300 is represented, showing how CO varies with the breath cycle, where the peak CO value corresponds to the end-tidal period. The peak CO value 310 is the value of interest, as it is the most closely correlated to the CO level in the blood. In the capnometry example 330 in FIG. 3B, time and amplitude threshold values are established to determine the beginning and end of the end-tidal period. YA and YB are the $CO_2$ amplitudes at the slope transition point and peak level respectively, representing the beginning and ending end-tidal $CO_2$ amplitudes respectively. XA and XB are the durations of the pre-end-tidal period and expiratory period respectively, measured from t1', the start of the expiratory period as defined by an increase from the baseline CO2 level. Thresholds Y1, Y2, X1 and X2 can be respectively established from and based on trending, averaging, pattern recognition or other protocols of YA, YB, XA and XB, for example a percentage of a moving average trended value with exceptions disregarded. In the airway pressure example 360 of FIG. 3C, YC represents the peak amplitude, corresponding to the start of the end-tidal period, and XA and XB represent the duration of the pre-end-tidal period and the expiratory period. Thresholds X1, X2 and Y1 are established from and based on trending, averaging, pattern recognition or other protocols of XA, XB and YC respectively, and threshold Y2 is established base on the zero pressure. For example, end-tidal gas sample collection can begin, with the appropriate phase shift, when nasal pressure reaches the peak value, or Y1, or at the midpoint of expiratory phase, XB/2, based on trending, reaches zero, and end when nasal pressure becomes negative, or zero, or when it reaches Y2, or after a time delay of XB, or after a time delay based on previously measured expiratory time. Measuring breathing airflow or proximal airway temperature provides very similar information to airway pressure, and these signals can also be used in the manner previously described to determine the different portions of the breathing curve and the end-tidal period. In addition other breath measurements can be made to discern the breathing pattern, such as sound, ultrasound, vibrations, and plethysmography.

The threshold techniques described in FIGS. 3B and 3C can be highly reliable when the breath pattern is relatively constant and non-erratic. However, in non-constant or erratic breathing situations, capnometry and airway pressure may not reliably distinguish the beginning and end of the end-tidal period. For example capnometry may have difficulty in reliably identifying exactly the transition between the pre-end-tidal and end-tidal periods, because this transition may look different for different breathing patterns. For example, the slope of $CO_2$ increase during the expiratory phase may be constant without the transition point from a first slope to a second slope in FIG. 3B. Or, there may be more than two $CO_2$ slopes during the expiratory phase hence more than one transition, making it potentially arbitrary to determine which slope transition corresponds to the beginning of the expiratory phase. The foregoing are merely examples of potential difficulties in identifying the beginning of the end-tidal period, and other issues are possible. A proximal airway pressure signal, with the appropriate algorithms, may improve reliability over capnometry in that rarely would there be more than one peak exhalation pressure for a given breath, making this marker a reliable marker. Similarly, the transition from positive pressure to zero pressure, with the appropriate zeroing algorithms, may reliability correlate to the end of the end-tidal period. Therefore, using proximal airway pressure sensing may provide enhanced fidelity and in addition may substantially lower cost. Nonetheless, airway pressure may also be limited in its fidelity.

Figure 4A:
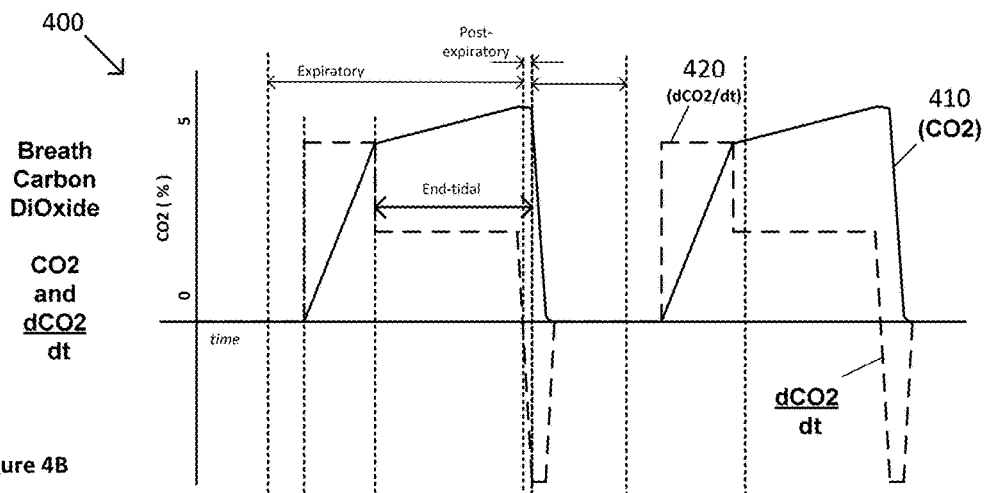
FIG. 4A describes a capnometry signal for different phases of the breathing cycle and one variation of a differential of the signal for identifying different portions of the breath.
Figure 4B:
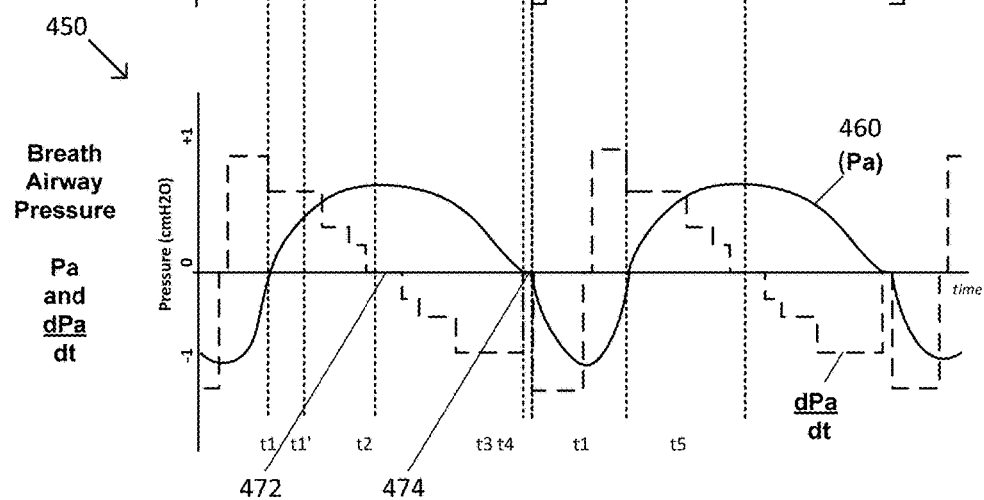
FIG. 4B describes an airway pressure signal for different phases of the breathing cycle and one variation of a differential of the signal for identifying different portions of the breath.

FIGS. 4A and 4B indicate another variation using capnometry and proximal airway pressure to measure the breathing pattern and identify different portions of the breathing pattern, including the end-tidal period. FIG. 4A is a graph 400 of exhaled carbon dioxide and the rate of change (first derivative) of exhaled carbon dioxide. ($CO_2$ is represented by line 410 and the derivative of $CO_2$ is represented by line 420.) In FIG. 4A the breath $CO_2$ is measured and the measurement is differentiated instantaneously in real time. By observing instant changes in slope and comparing against the appropriate threshold values (such as the threshold values described herein), the start of the end-tidal period can be reliably identified. And by observing rapid changes from a positive to a negative differentiated value, the end of the end-tidal period can be reliably identified. In addition to distinguishing the end-tidal period, other portions of the breath phase can be identified using this technique. In other variations, a second differential of the measured signal can be utilized to further improve the fidelity or reliability of identifying an exact portion of the breath pattern.

FIG. 4B is another variation using measured proximal airway pressure, differentiated in real time. FIG. 4B is a graph 450 of proximal airway pressure and the rate of change (first derivative) of the proximal airway pressure. (Airway pressure is represented by line 460 and the derivative of airway pressure is represented by line 470.) A first zero value 472 of dPA/dt subsequent to a positive value indicates the peak airway pressure at time t2 corresponding to the start of the end-tidal period. A second zero value 474 of dPA/dt subsequent to a negative value indicates a zero airway pressure value at time t3 corresponding to the end of the expiratory end-tidal period. In addition to manipulating a capnometry or airway pressure signal in this manner, other breath parameters can be likewise manipulated. Examples of such other parameters include breathing gas temperature, humidity, airflow, sound and others. Although end-tidal CO gas analysis is described in the examples herein, it should be understood the systems and methods can apply to sampling and analyzing other gases from other portions of the breathing cycle.

For some breath analysis applications, a minimum quantity of gas volume is required by the gas composition analyzer in order for it to provide an accurate analysis. One technique for obtaining the gas sample for analysis is to collect the gas in a temporary storage compartment while it is being drawn from the patient. The storage compartment is sized to a known volume to meet the volume requirement of the gas composition analyzer, and for convenience, the compartment can be a fixed or constant volume. After the compartment is filled with the desired gas, the gas in the compartment can then be sent to the composition analyzer for analysis. The gas stored and analyzed may be purely from the targeted portion of exhalation in order to achieve an accurate analysis. Therefore, the system may be capable of obtaining that volume of gas from the correct part of the breath, under a wide variety of breathing patterns, and yet still collect the requisite quantity of gas for the analyzer to be accurate.

Figure 5A:
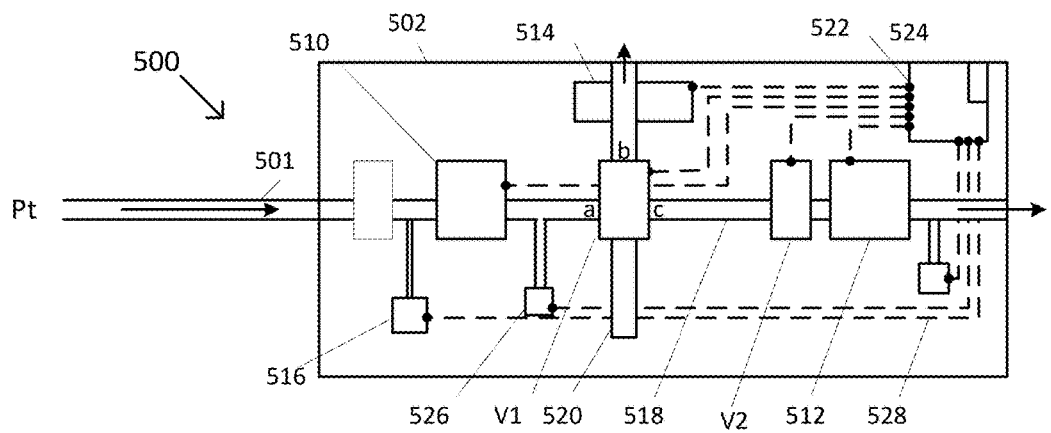
FIG. 5A describes schematically an overview of one variation of a breath capturing system.

FIG. 5A describes schematically an overview one variation of a device for capturing exhaled breath, including a sampling cannula 501 and a gas sample collection and analysis instrument 502. Gas may be drawn from the patient, for example using the sampling cannula 501 and a flow generator 512. The flow rate of the flow generator may be measured by a flow transducer, for example a pressure sensor array, 526 and 528, arranged similarly to pneumotach. The measured flow rate may be used as a closed loop feedback control to control the flow generator flow rate. A breath sensor, such as a capnometer 510 or a pressure sensor 526, may be used to measure the breathing pattern in real time. Gas from the desired portion of the breath is captured and isolated in the storage collection compartment 518. Gas entering the storage compartment is controlled by at least one valve V1, for example with a common port c always open, and a second open port, either a to collect gas or b to isolate the storage compartment. There may be a valve V2 between V1 and the flow generator to participate with V1 in isolating the storage compartment. Gas not being captured for analysis is channeled away from the storage compartment via a bypass conduit 520. The captured gas is sent from the storage compartment through a gas composition analyzer 514, such as a CO sensor. A control system 522 with a microprocessor 524 controls the system with the associated algorithms. The flow generator can be a vacuum or pressure pump, such as a diaphragm pump, or another type of flow generating device such as a vacuum source, a Venturi from a positive pressure source, or a syringe pump. Valves to manage gas routing can be an arrangement of 3 way 2 position valves or can be an arrangement of 4 way 3 position valves. Capnometer 510, if used, measures the breathing pattern instantaneously using infrared (IR). The gas composition analyzer can be an electrochemical sensor with a reaction time, or a gas chromatographer, or a mass spectrometer. Other variations may use different analyzers. The sample storage compartment can be a small bore inner diameter tube or conduit of considerable length in order to minimize the cross section which may reduce gas molecule interaction along the length of the conduit. The sampling cannula may be a silicone or PVC tube with an inner diameter of 0.020-0.080". Pressure sensor 516 is an additional pressure sensor that may be used in tandem with 526 so that a flow rate can be determined, in addition to using it for airway pressure measurement. Flow rate can be used to adjust the pump speed in some variations that utilize a variable flow rate. Pressure sensor 516 can also be utilized for ambient information where the breathing curve is measured by pressure instead of capnometry. In some variations, an instantaneous carbon monoxide sensor is used as the breath sensor, in place of a capnometer or an airway pressure sensor. Other instantaneous breath sensors may also be used.

Figure 5B:
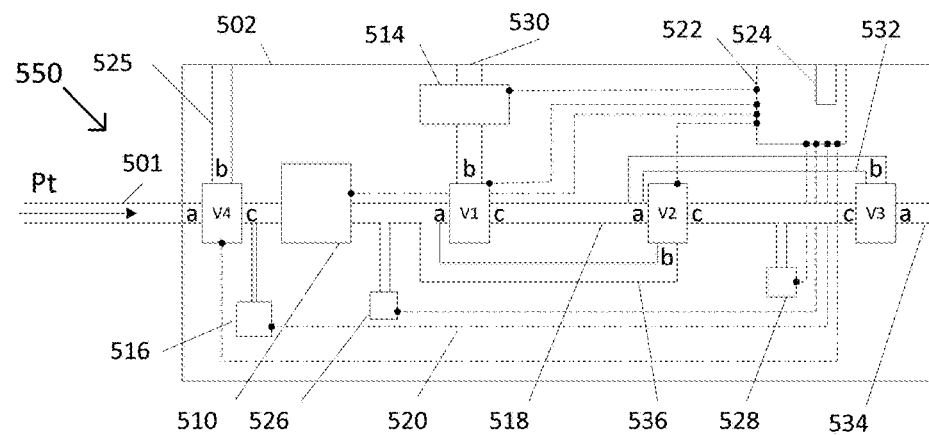
FIG. 5B describes schematically an overview of another variation of a breath capturing system.

FIG. 5B describes additional details about the pneumatic operation of the system shown in FIG. 5A (see also FIG. 9C below). For similar features in FIG. 5A, a discussion is not repeated here. A bypass tube 536 allows the gas being drawn from the patient or from ambient to bypass the sample tube 518 during times which the sample tube may be isolated from these gases. In this arrangement, valve V1 may be closed at port a and valve V2 may be open at port b to allow flow from b through c. A flow generator may be used to draw the sampling gas through the bypass type. A push tube 532 may be used to push the end-tidal sample in the sample tube 518 out of the sample tube to the sensor 514, at which time valves V1 and V3 are each open at port b and V2 is closed at port a. Valve V4 switches the source gas from patient gas to ambient gas by opening port b, when it is desired to not contaminate the internal gas pathways with patient gas or for purging the system.

In some variations, the pneumatic system shown in FIGS. 5A and 5B above may include a removable sampling compartment (not shown). For example, sample tube 518 may be removable form the system. In this way, the pneumatic system may be able to fill a sample tube with a desired gas, and the sample tube may be analyzed at another location, or preserved for later analysis. In other variations, the gas may be routed from the sample tube to a removable sampling compartment. In this variation, the compartment may replace the analyzer or otherwise be positioned so that it can be removed and/or replaced.

Figure 6:
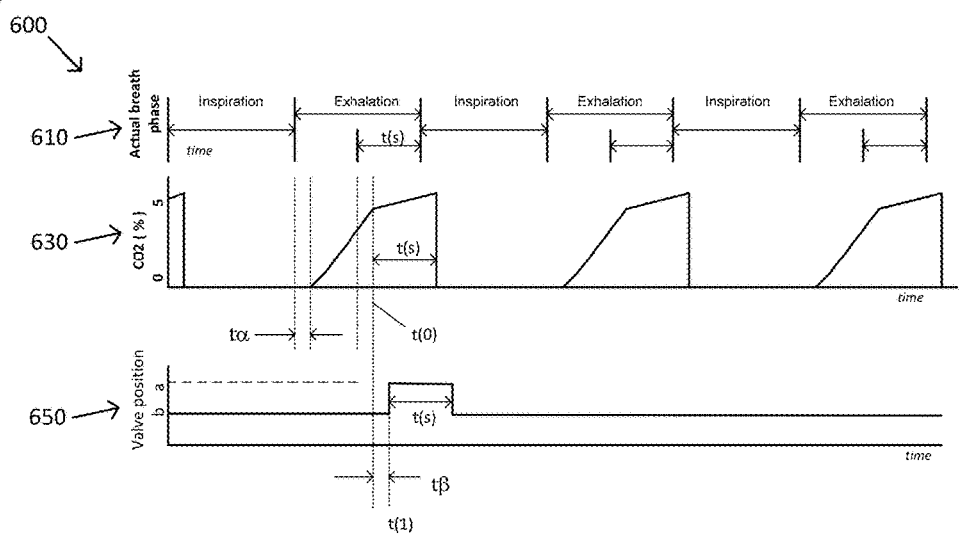
FIG. 6 provides a collection of graphs illustrating the phase shift associated with using capnometry to identify and collect a breath sample.

FIG. 6 provides a collection 600 of graphs illustrating the phase shift associated with using capnometry to identify and collect a breath sample in one variation of a device for capturing exhaled breath. The top graph 610 illustrates actual breath phase (inspiration/expiration). The middle graph 630 illustrates $CO_2$ concentration. The bottom graph 660 illustrates valve position. The travel time for gas to travel from the person to the capnometer through the sampling cannula is represented by $t\alpha$. Therefore the capnometry signal shows a beginning of exhalation slightly after the true beginning of exhalation. The travel time for the gas to exit the capnometer and begin to enter the sample collection compartment is represented by $t\beta$. Therefore the sample compartment isolation valve V1 opens to position at a time t(1), $t\beta$ after detection of the start of the end-tidal period by the capnometer, for the sample collection time t(s).

Figure 7:
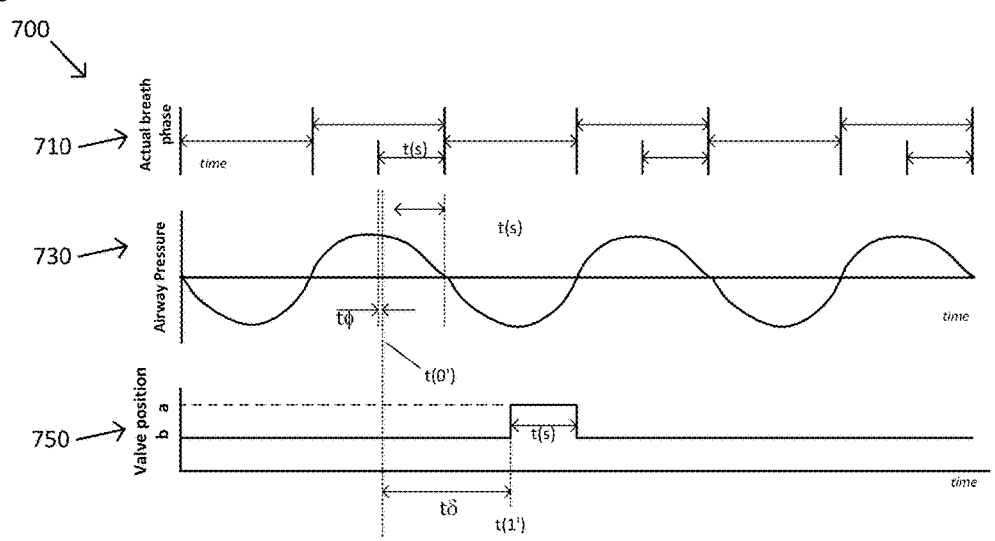
FIG. 7 provides a collection of graphs illustrating the phase shift associated with using airway pressure monitoring to identify and collect a breath sample.

FIG. 7 provides a collection 700 of graphs illustrating the phase shift associated with using airway pressure monitoring to identify and collect a breath sample in one variation of a device for capturing exhaled breath. The top graph 710 illustrates actual breath phase (inspiration/expiration). The middle graph 730 illustrates airway pressure. The bottom graph 750 illustrates valve position. The phase shift between the actual breath, and the pressure is $t\phi$, approximately equal to the distance of travel divided by the speed of sound, hence is relatively instantaneous. The travel time for the gas to exit the person's airway and begin to enter the sample collection compartment is represented by $t\delta$. Therefore the valve V1 opens to position a at time t(1'), which is $t\delta$ after detection of the start of the end-tidal period by the capnometer, for the sample collection time t(s).

In the following discussion, reference is made to the device for capturing exhaled breath described above with respect to FIGS. 5A and 5B. It should be noted that other devices could be used to determine a duration of a period of an exhaled breath and capture that period of breath without deviating from the scope of the disclosure.

Figure 8:
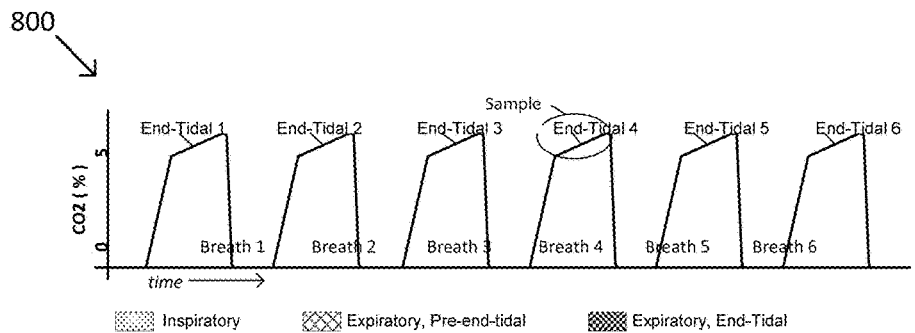
Figure 9A:
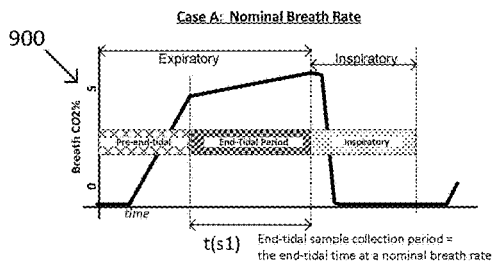
FIG. 9A is a graph of a breath capnometry waveform representative of a nominal breath rate.
Figure 9B:
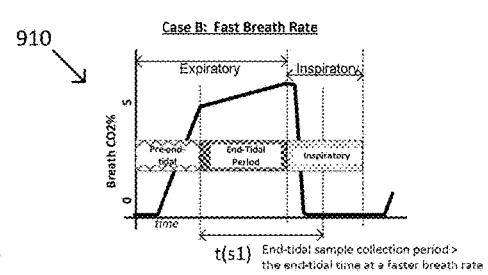
FIG. 9B is a graph of a breath capnometry waveform representative of a relatively fast breath rate.
Figure 9C:
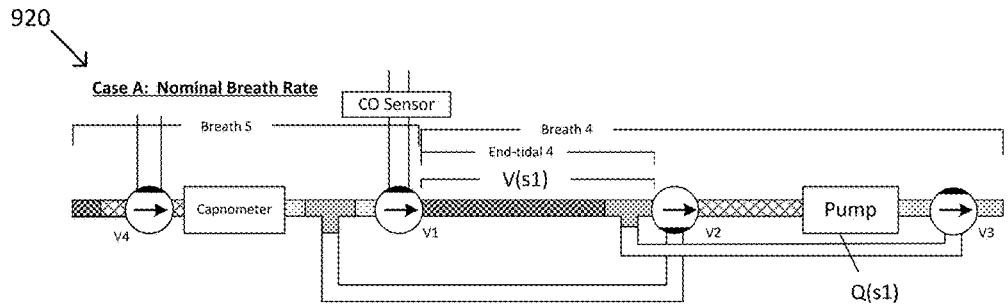
FIG. 9C describes the system of FIG. 5A or 5B capturing an end-tidal gas sample from the breath shown in FIG. 9A.
Figure 9D:
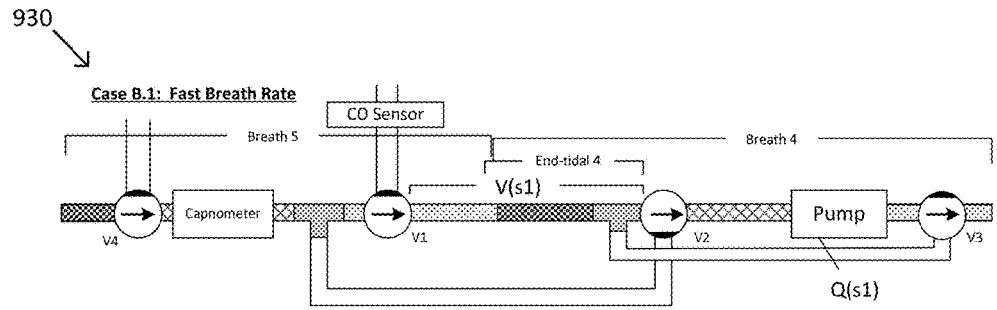
FIG. 9D describes the system of FIG. 5A or 5B capturing an end-tidal gas sample from the breath shown in FIG. 9B.
Figure 9E:
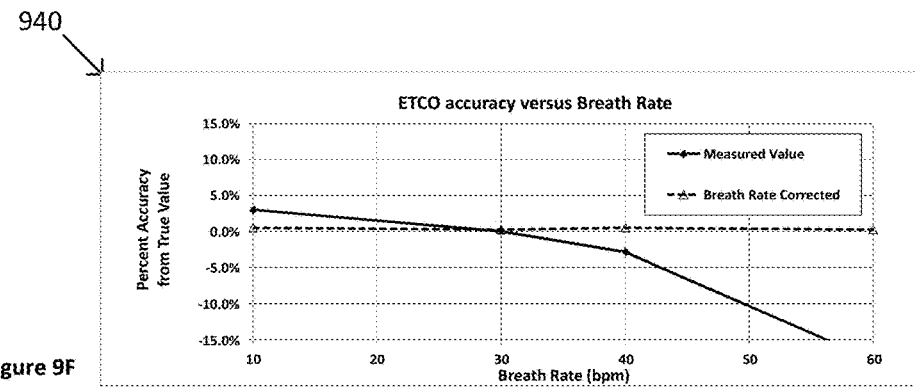
FIG. 9E shows use of a breath rate correction factor to compensate for non-homogeneity of the captured gas sample, using a breath simulator and known CO gas input, with and without a correction factor applied.
Figure 9F:
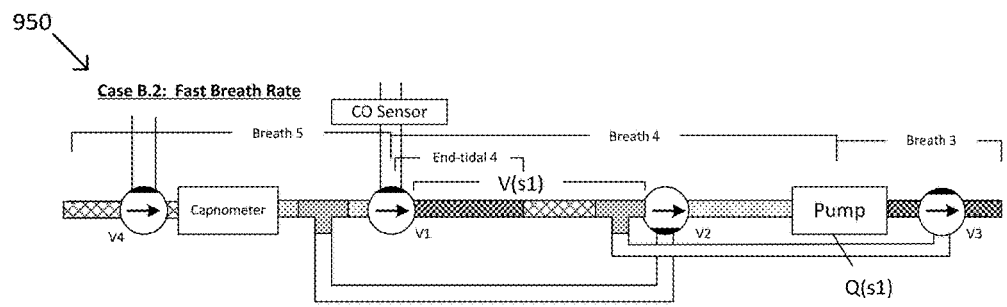
FIG. 9F describes an alternate configuration of the system shown in FIG. 9D in which the end-tidal sample is placed in the valve V1 side of the sample tube.
Figure 9G:
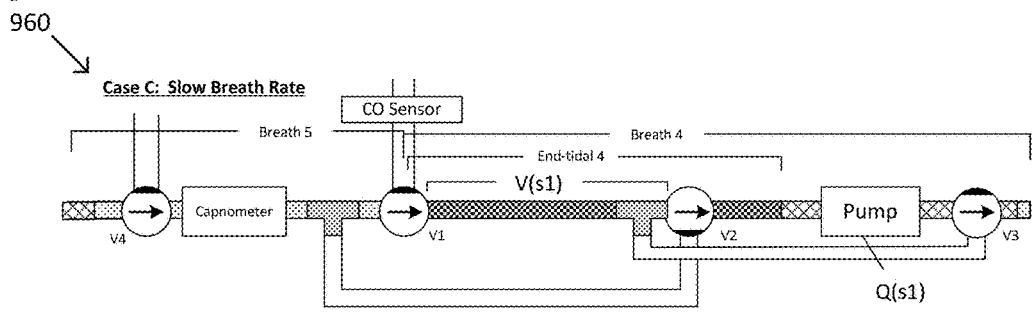

In a first variation of a breath-rate-modulated variable, shown in FIGS. 8-9G, a correction factor is applied to the gas composition analysis result to compensate for non-homogeneity of the captured gas sample. The system in the example shown analyzes end-tidal CO gas by identifying the end-tidal period using capnometry, and uses a fixed gas sampling time and sampling flow rate. FIG. 8 is a graph 800 of a capnometry signal for a series of breaths. The capnometry signal is used to identify a good breath to sample and to identify the end-tidal period, with the most recent breath on the right end, and the oldest breath on the left end of the graph. Breaths 1 through 3 are monitored and assessed for meeting a qualification criteria, and if met, the end-tidal portion of breath 4 is sampled for analysis.

FIG. 9A is a graph 900 of a nominal case corresponding to FIG. 8 in which breath number 4's end-tidal period matches the sampling time t(s1). FIG. 9C illustrates the arrangement 930 of a pneumatic system for capturing the gas described in the nominal case shown in FIG. 9A, in which gas from the end-tidal period of Breath 4 completely fills the sample collection compartment volume V(s1). In FIG. 9C, the pre-end tidal of Breath 4 can be seen to the right of V2, out of the sample compartment. The inspiratory portion of Breath 5 can be seen to the left of V1, out of the sample compartment.

In the graph 910 of FIG. 9B, the sampling time t(s1) is greater than the end-tidal period. The arrangement 940 shown in FIG. 9D, corresponding to the graph of FIG. 9B, comprises both end-tidal gas from breath 4 and inspiratory gas from breath 5. For example, if the system is tuned for a 1 second end-tidal time with a sample collection time of 1 second, and the actual end-tidal time is 1 second, then the sample gas is homogeneous with respect to the different portions of the expiratory phase, and the analysis may be most accurate (see FIGS. 9A and 9C). However, if the person's end-tidal period becomes shorter or longer in duration, the sample compartment may miss some of the end-tidal gas or may include some non-end-tidal gas, respectively, which may inevitably lead to inaccuracies in the analysis, which can be corrected for by application of the gas heterogeneity breath-rate correction factor. For example, if the end-tidal time is 0.5 seconds, the sample compartment may be 50% filled with pure end-tidal gas from the entire end-tidal period plus 50% filled with inspiratory gas, thereby diluting the concentration of the CO in the sample compartment. Assuming the CO of the gas sample from inspiratory phase is known, for example 0.25 ppm, and assuming the analyzer's measurement result is 1.25 ppm CO, and the known ambient CO is 0.25 ppm, then the sample contains 50% of 0.0 ppm CO, and 50% of 1.0 ppm CO for a corrected CO of 0.5 ppm CO. In this case the correction factor is 0.5. In the example shown in FIG. 9B, the sampling time t(s1) is greater than the end-tidal period. The captured gas sample shown in FIG. 9D corresponding to FIG. 9B comprises both end-tidal gas from breath 4 and inspiratory gas from the next breath.

The resultant CO analysis at 60 bpm shown by the solid line in the graph in FIG. 9E shows a 15% error due to dilution of the sample, however application of the breath rate dependent correction factor shown by the dotted line achieves 2% accuracy in this example. The correction factor may be a linear equation with a slope and offset value applied to all breath rates across the operating range of the device.

FIG. 9E describes a graph 950 of accuracy versus breath rate from an end-tidal CO analyzer, using a breath simulator and a known CO gas concentration input, and a mathematical correction formula. The solid curve in the graph 950 in FIG. 9E at 40 bpm describes the resulting accuracy of the CO analysis of the sample collected. In the example shown, the sample tube volume and gas sample flow rate are sized and set respectively to completely fill the sample tube of end-tidal gas from the complete end-tidal period, for an end-tidal period of 500 milliseconds corresponding to 30 breaths per minute with a 1:1 I:E ratio ("Inspiratory:Expiratory"). As can be seen in the graph, the curve is very accurate at breath rates below 30 bpm, because at 30 bpm the sample tube is completely filled with homogenous end-tidal gas, and below 30 bpm, the sample tube is also filled with homogenous end-tidal gas, although not from the entire end-tidal period. However, above 30 bpm, the sample tube comprises gas from the entire end-tidal period of the breath sampled, plus some gas from before or after the end-tidal period because the end-tidal periods at these breath rates are shorter in duration than the gas sampling time, therefore resulting in a negative slope in the curve due to the dilution. As can be seen in the corrected curve, the results at breath rates greater than 30 are accurately adjusted with the correction factor. The accuracy between 10 and 30 bpm may not be linear because at 10 bpm the sample tube contains the very end of the end-tidal gas, which might be slightly higher in CO concentration than the average throughout the end-tidal period, whereas at 30 bpm, the sample tube contains the gas from the entire end-tidal period. The general equation describing the relationship between measured and actual gas is x=My+B, for example x=0.0074y+0.07, where x is the measured ETCO, M is the slope of the equation, y is breath rate corrected ETCO, and B is the equation y intercept or offset. Therefore $ETCO_{(corrected)}=[ETCO_{(measured)}-\text{offset}]/\text{slope}$.

FIG. 9F describes an alternate configuration 960 of the system shown in FIG. 9D in which the end-tidal sample is placed in the valve V1 side of the sample tube. This is a similar configuration to FIG. 9D, except a portion of the expiratory end-tidal period of breath 4 is captured in the sample instead of the inspiratory phase (as shown in the configuration of FIG. 9D). FIG. 9G illustrates configuration 970 of the system of FIGS. 9C and 9D in which a breath is captured from a slow breath rate. In the configuration of FIG. 9G, some end-tidal gas is not captured in the sample tube in the area past V2.

Figure 10A:
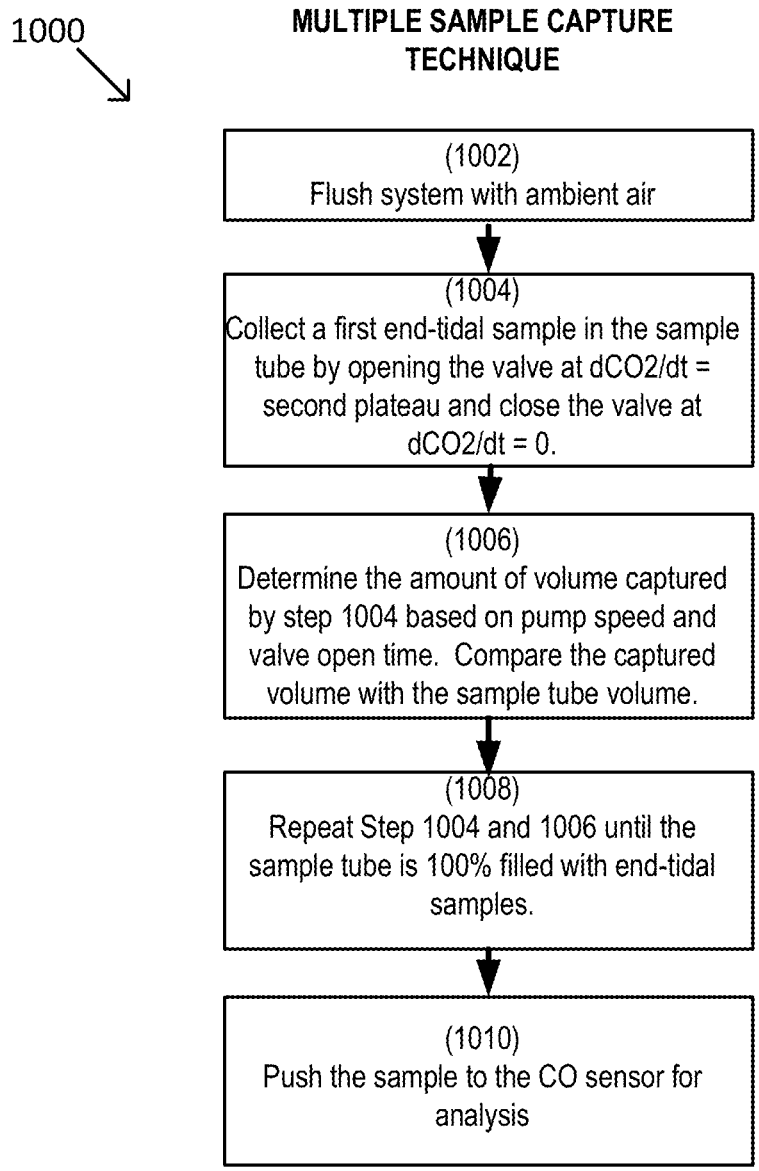
FIGS. 10A-10B describe one variation of a method of modulated multiple breath sampling for capturing a targeted volume of end-tidal gas and subsequent gas analysis.

FIG. 10A illustrates a method 1000 for sampling multiple breaths to collect a targeted volume of end-tidal gas. Method 1000 optionally begins with step 1002, flushing the system with ambient air. This may not be necessary every time the method is performed. Method 1000 continues with collecting a first end-tidal sample 1004. A valve on a sampling tube is opened at the appropriate time to correlate with the beginning of the end-tidal period. The variation depicted in FIG. 10A indicates the valve is open to correlate with a second plateau of the first derivative of the carbon dioxide concentration, but other variations may use alternative triggers for the beginning of the end-tidal period, such as those described in this disclosure. The valve on a sampling tube is closed at the appropriate time to correlate with the end of the end-tidal period. The variation depicted in FIG. 10A indicates the valve is closed to correlate with a zero of the first derivative of the carbon dioxide concentration, but other variations may use alternative triggers for the end of the end-tidal period, such as those described in this disclosure. The method with step 1006 to determine the volume of gas captured in step 1004. The variation depicted in FIG. 10A indicates the volume based on the pump speed and valve open time, but other mechanisms could equivalently be used. The captured volume is then compared to the sample tube volume to determine if the sample tube is filled. If not, Step 1008 repeats the capturing step of 1004 and the comparison of step 1006 until the sample volume is filled. Then the method, in step 1010, pushes the collected volume to a CO analyzer. In some variations, the collected volume may be pushed to a different type of gas analyzer, or pushed to a removable storage tube for delivery to a lab or other analyzing facility.

Figure 10B:
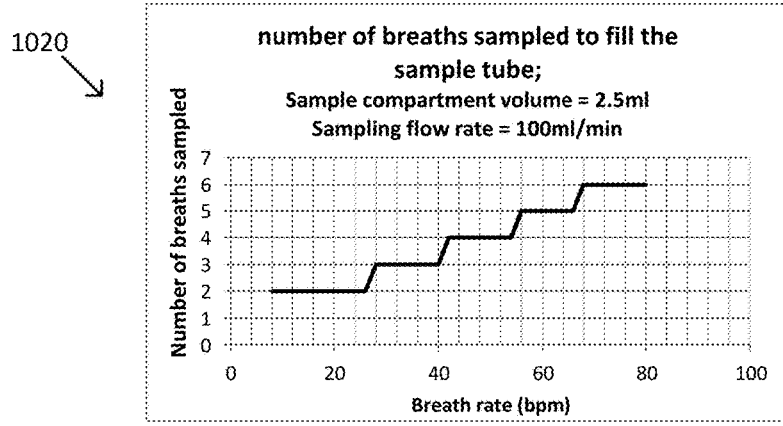

As described above, in order to compensate for any breath rate or breath pattern and still obtain the desired sample volume and gas purity, multiple breaths may be sampled. The number of breaths will depend on the breath pattern and the compartment volume. FIG. 10B illustrates a graph 1020 of the number of breaths that may be necessary to fill a sample volume. For exemplary purposes, the sample compartment is 2.5 ml, the sample flow rate is 100 ml/min, and assuming end-tidal gas is being analyzed, 3 breaths are needed to be sampled for example at a breath rate of 30 breaths per minute, etc. It should be understood that varying the sample compartment, flow rate, etc. may lead to a different graph. Graph 1020 provides an easy reference to determine how many breaths may be necessary to fill the compartment tube. Although the variation of FIG. 10B depicts breaths sampled as whole numbers (and, thus, a step-function graph), other variations may use a continuous graph line, thereby indicating that a partial breath (in addition to one or more full breaths) will be captured to fill the sample volume. This information may be utilized to close the sample compartment valve at an appropriate time.

FIGS. 11A-11F graphically describe the method of FIGS. 10A-10B using the apparatus of FIG. 5A or 5B, for explanatory purposes. It should be noted that any number of apparatuses could be used to capture a specific portion of breath without deviating from the scope of the present disclosure.

Figure 11A:
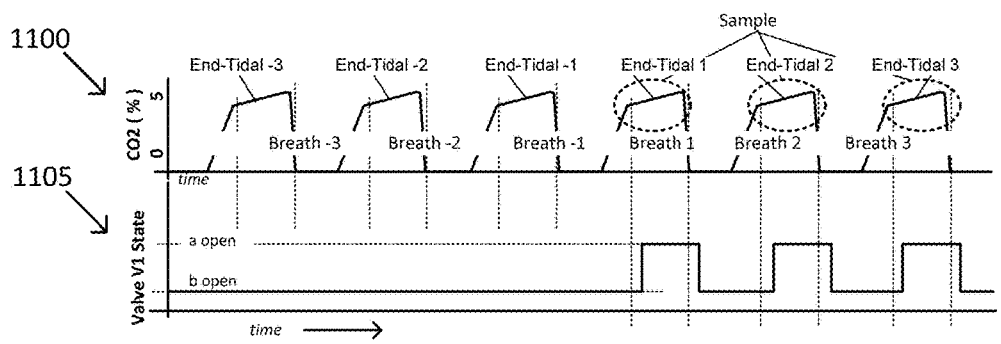
FIGS. 11A-11F describe one variation of a breath-rate-modulated multiple breath sampling technique for capturing a targeted volume of end-tidal gas and subsequent gas analysis.
Figure 11B:
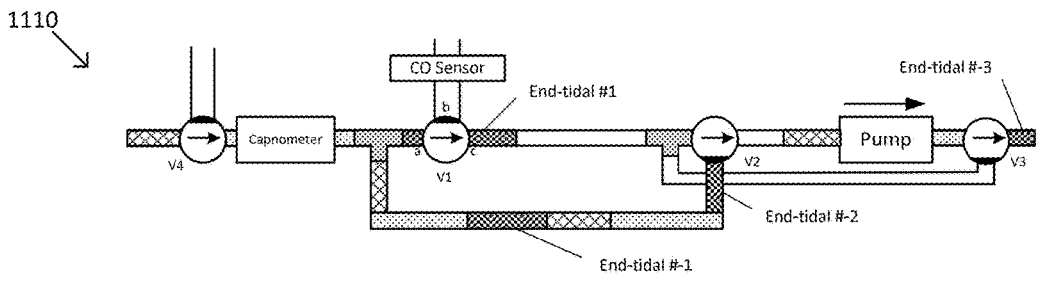
Figure 11C:
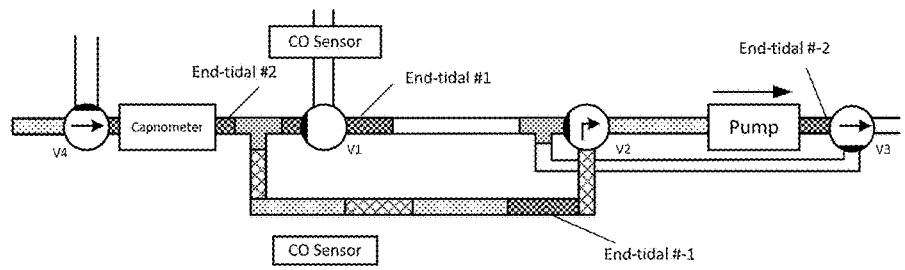
Figure 11D:
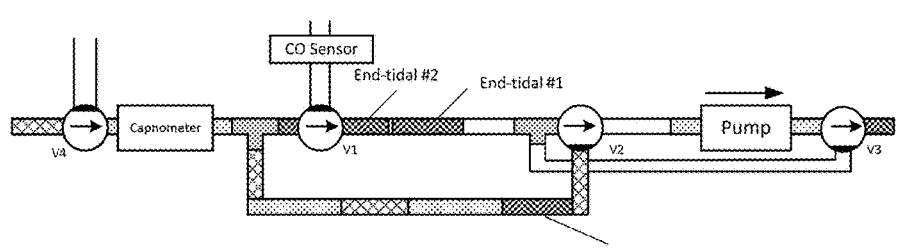
Figure 11E:
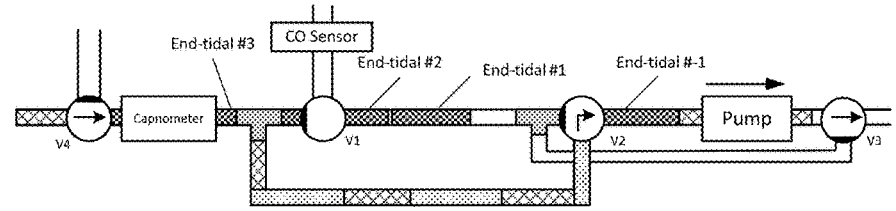
Figure 11F:
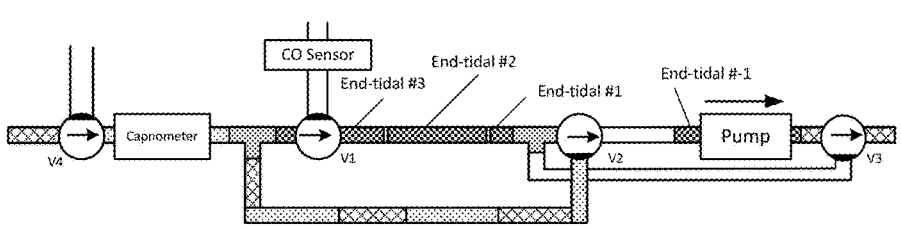

FIG. 11A illustrates a graph 1100 showing the carbon dioxide levels of a series of breaths. After identifying and assessing the first three breaths, the system decides to begin collecting samples from the fourth breath, labeled breath 1. Depending on the prevailing breath pattern, the appropriate number of end-tidal periods are sampled to collect the requisite volume. The breaths may be first verified that they meet necessary criteria for sampling, resulting in either multiple consecutive breaths, or non-consecutive breaths. FIG. 11A also illustrates a graph 1105 of the valve state of the valve V1 on the inlet to the sample tube. While the first three breaths ("breath −3" to "breath −1") are verified, the inlet to the sample tube is closed ("b open"). When the system determines to sample breath 1, the inlet to the valve is opened ("a open") to allow the sample tube to collect the end-tidal period of breath 1. As can be seen in FIG. 11A, there is a phase shift (time offset) from the beginning of the end-tidal period to the opening of the inlet valve. This may reflect a finite time required for the breath to travel from the patient to the inlet valve, as described above. When the end-tidal period is over, the inlet valve is again closed. The open and closing of the inlet valve is then repeated for two further breaths.

After storing each sample, before the next sample is stored, the gas being drawn from the patient is channeled to bypass the storage compartment. These configurations of the system is illustrated in FIGS. 11B to 11F. In configuration 1110 of FIG. 11B, gas from the first breath's end-tidal phase begins to be stored in the sample tube. In configuration 1120 of FIG. 11C, the gas after the first breath's end-tidal phase (i.e., the second breath's inspiratory and pre-end tidal phases) is channeled through the bypass tube. In configuration 1130 of FIG. 11D, gas from the second breath's end-tidal phase begins to be stored in the compartment. In configuration 1140 of FIG. 11E, the gas after the second breath's end-tidal phase (i.e., the third breath's inspiratory and pre-end tidal phases) is channeled through the bypass tube. In configuration 1150 of FIG. 11F, gas from a third breath's end-tidal phase begins to be stored in the compartment, after which the compartment is completely filled with pure end-tidal gas from multiple breaths. After this, sample collection can end, and the gas in the storage compartment can be sent to the gas analyzer for compositional analysis. In one variation the sample compartment can be volumetrically sized for a gas sample drawn from a single end-tidal period that is associated with the longest possible end-tidal duration imaginable. All other breath rates will result in sampling gas from more than one breath. In a further variation, in some clinical applications it might be desired to size the storage compartment so that the system always samples at least a few breaths or samples breathing for at least 30 seconds, in order to collect an average reading over a period of time, to dampen the effect of any breath-to-breath perturbations in the actual gas composition.

Figure 12A:
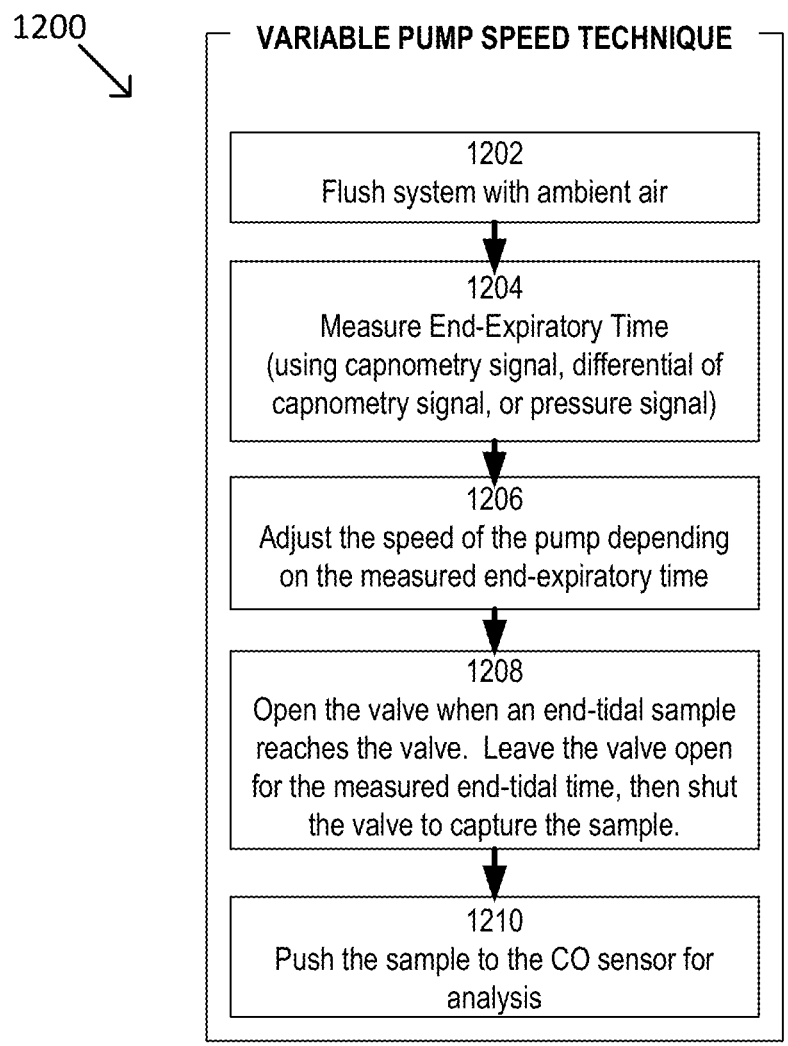
FIGS. 12A-B describe one variation of a method of modulated variable sampling flow rate for capturing a targeted volume of end-tidal gas and subsequent gas analysis.

FIG. 12A illustrates a method 1200 of capturing a breath using a variable pump speed to collect a targeted volume of end-tidal gas. Method 1200 optionally begins with step 1202, flushing the system with ambient air. This may not be necessary every time the method is performed. Method 1200 continues with measuring an end-expiratory time 1204. In the variation of method 1200, the end-expiratory time could be measured using a capnometry signal, differential of capnometry signal, or a pressure signal. In other variations, the end-expiratory time could be measured in a different way, such as those described herein. Method 1200 then continues with step 1206, adjusting the speed of the pump based on the measured end-expiratory time in step 1204. Method 1200 then continues to step 1208, where the valve is opened when an end-tidal sample reaches the valve. The valve may remain open for the duration of the measured end-tidal time, and then is shut to capture the sample when the end-tidal time has passed. Then the method, in step 1210, pushes the collected volume to a CO analyzer. In some variations, the collected volume may be pushed to a different type of gas analyzer, or pushed to a removable storage tube for delivery to a lab or other analyzing facility.

Figure 12B:
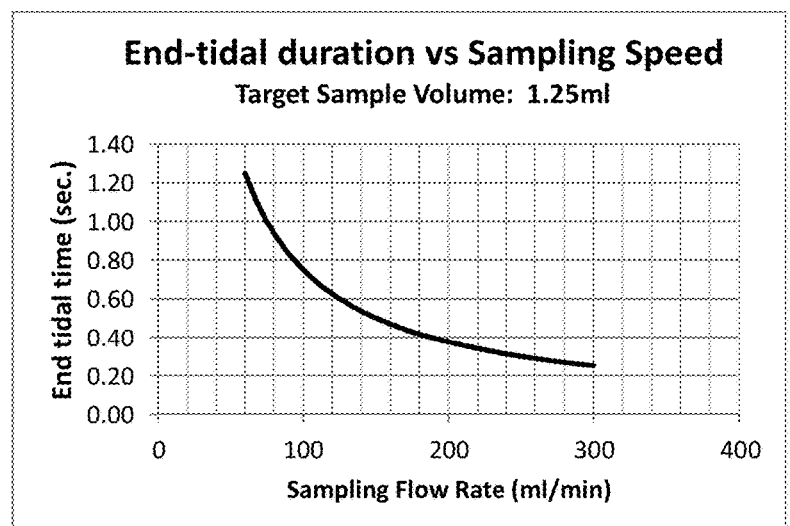

As described above, in order to compensate for any breath rate or breath pattern variability and still obtain the desired sample volume, the sample flow rate may be adjusted. FIG. 12B illustrates a graph 1220 of a sampling flow rate that corresponds to an end-tidal period. For exemplary purposes, the sample storage compartment is 1.25 ml and the end-tidal portion of a particular breath is 1 second in duration. In that example, the sample flow rate is adjusted to be 1.25 ml/second or 75 ml/minute in order to collect a 1.25 ml sample of gas sampled from the complete end-tidal period. It should be understood that varying the sample compartment, flow rate, etc. may lead to a different graph.

Figure 13A:
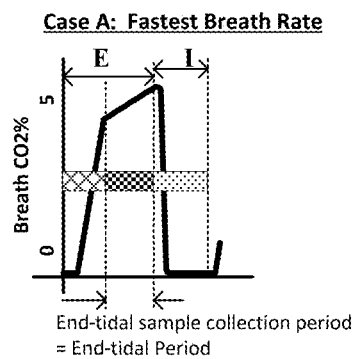
FIGS. 13A-13F describe one variation of a breath-rate-modulated variable sampling flow rate technique for capturing a targeted volume of end-tidal gas for subsequent analysis.
Figure 13B:
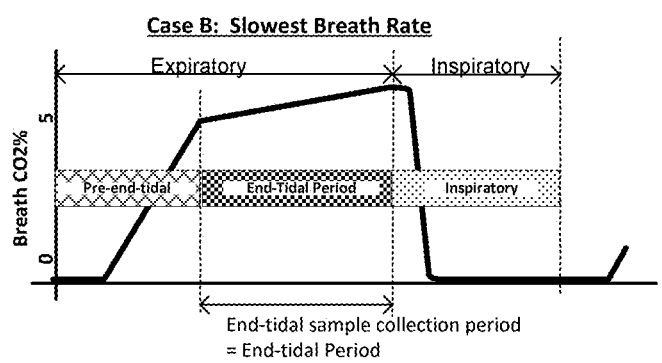
Figure 13C:
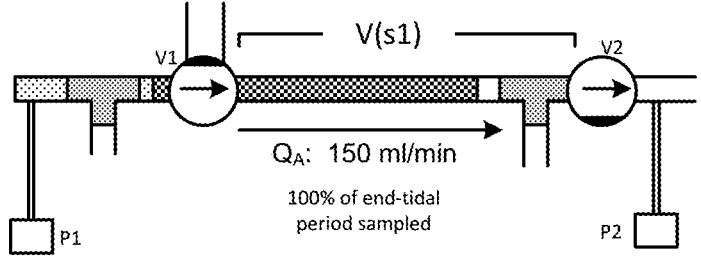
Figure 13D:
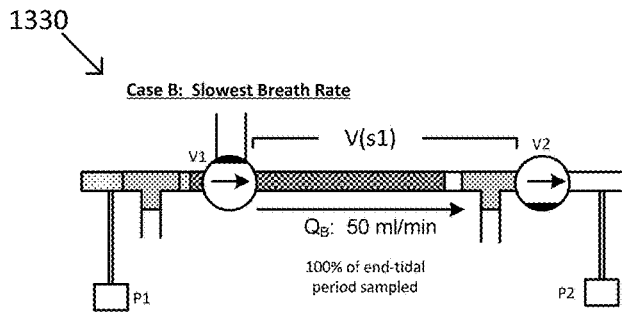

FIGS. 13A-13F describe the method of FIGS. 12A-12B using the apparatus of FIG. 5A or 5B, with two breathing cases for comparison. It should be noted that any number of apparatuses could be used to capture a specific portion of breath without deviating from the scope of the present disclosure. Graph 1300 in FIG. 13A represents "Case A," a relatively fast breath. Graph 1310 in FIG. 13B represents "Case B," a relatively slow breath. Case A and B result in relatively short and long end-tidal times respectively. In configurations 1320 and 1330 of FIGS. 13C and 13D, respectively, the system has a fixed sample compartment volume, V(s1), for example 1.0 ml. It will be understood that other volumes of sample tubes may be used without deviating from the scope of the disclosure. In Case A (FIGS. 13A and 13C), the end-tidal duration is 0.4 seconds and hence the sampling flow rate is adjusted to 150 ml/min, in order to draw a 1.0 ml gas sample in 0.4 seconds. In Case B (FIGS. 13B and 13D), the end-tidal duration is 0.833 seconds and hence the sampling flow rate is adjusted to 50 ml/min in order to draw a 1.0 ml gas sample in 0.833 seconds. Therefore, in both Case A and B, the entire end-tidal period is sampled for analysis, rather than just a portion of the end-tidal period, and the sample collection compartment contains pure end-tidal gas and is 100% filled with end-tidal gas. The correct amount of gas, 1 ml, may be sent to the gas CO analyzer in both cases for an accurate analysis. In other embodiments, the gas may be pushed to a different type of gas analyzer, or pushed to a removable storage tube for delivery to a lab or other analyzing facility. The speed of the pump can be precisely regulated by modulating the voltage or current driving the pump, based on look up tables in associated software. In some embodiments, the speed of the pump may be precisely regulated using a closed loop feedback control system by measuring the flow rate of the fluid, for example using a pneumotach as described in FIGS. 5A and 5B, and adjusting the speed of the pump by adjusting the current based on the measured flow rate. In some embodiments, a look up table may be used to apply a current to the pump depending on the desired flow rate, then, in addition, a pneumotach feedback loop may be used to make fine adjustments to the current to precisely obtain the exact flow rate needed.

Figure 13E:
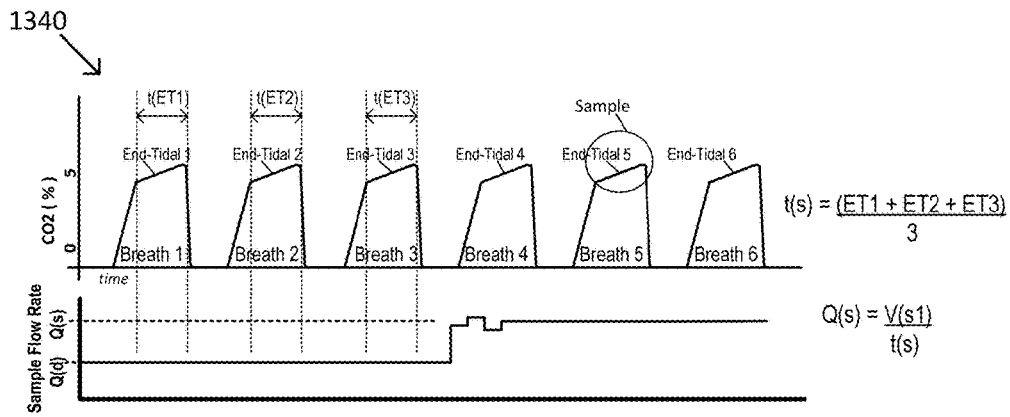

FIG. 13E illustrates a graph 1340 which describes the variable sampling flow rate technique of FIG. 12A when capnometry is used to measure the breathing pattern, showing a series of breaths with the most recent breath on the right end of the graph. After determination of an average end-tidal time from a series of preceding breaths (Breaths 1-3), the sample flow rate is adjusted from a baseline default sampling flow rate of Q(d) to sampling flow rate of Q(s), equal to the compartment volume V(s1) divided by the projected end-tidal time or sampling time t(s). Using the closed loop control of the flow generator, the flow is fine tune adjusted until it equals Q(s) (during Breath 4). Then gas from the end-tidal period of a subsequent breath (Breath 5)

is drawn at flow rate Q(s) and brought into the sample collection compartment. Additionally, the end-tidal time of the breath that was sampled can be measured to confirm it was equal to t(s) in order to validate the integrity of the sample. If the breath was erratic not conforming to t(s), then the sample can be discarded and the procedure repeated.

Figure 13F:
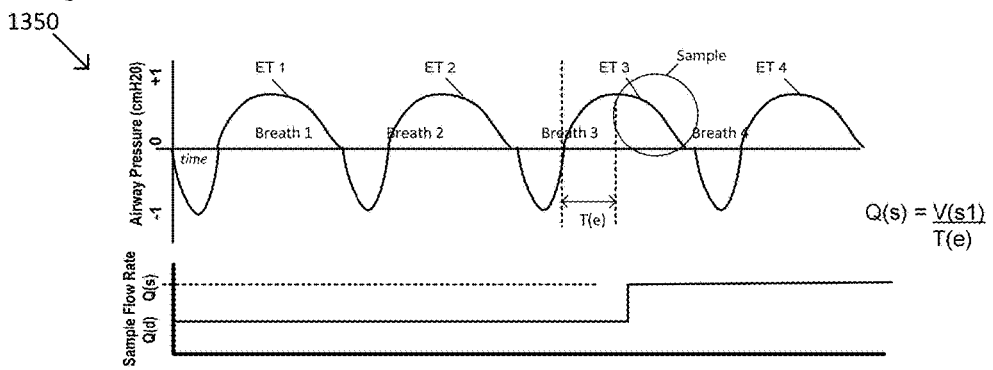

FIG. 13F illustrates a graph 1350 which describes the variable sampling flow rate technique of FIG. 12A when using airway pressure to measure the breathing pattern, showing a series of breaths with the most recent breath on the right end of the graph. In the example shown, end-tidal gas from breath 3 is sampled for analysis. The sample flow rate can be adjusted in a variety of ways. In one variation, the end-tidal time can be predicted from earlier breaths and the flow rate adjusted accordingly prior to drawing the sample from the targeted breath. In other variations, an adjustment to the flow rate can be made instantaneously based on the pre-end-tidal duration T(e) after T(e) is measured and known.

In some variations, a measured gas concentration may be adjusted to approximate an actual gas concentration. Such adjustments may account for variations in the fidelity of a breath sampling apparatus over a range of breath rates. The measured concentration may be modified using a correction equation, which may be specific to the apparatus being used, but may also be usable across various apparatuses. In some variations, the correction equation is formulated to cover a range of breath rates. In some variations, a breath rate and a measurement of a gas concentration in the apparatus may be sufficient to approximate the actual concentration of the gas at an inlet of the apparatus using a correction equation.

Figures 14A, 14B:
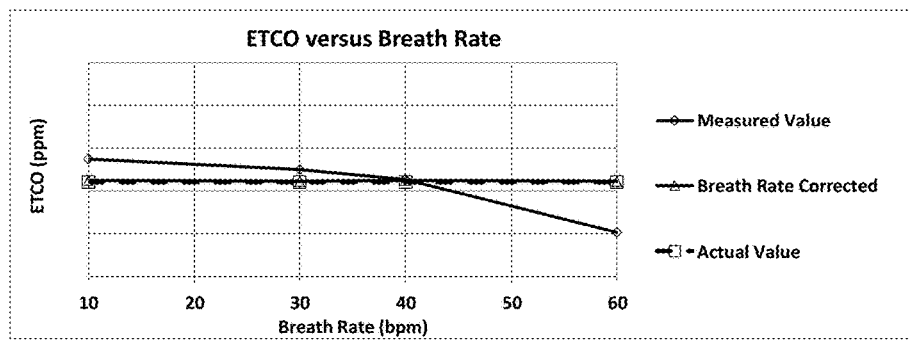
FIGS. 14A and 14B describe derivation and use of correction factor equations to adjust for the heterogeneity of end-tidal gas.

FIG. 14A is a graph 1400 illustrating ETCO ppm as a function of breath rate. In the example shown the actual ETCO ppm is 4.1 ppm. Graph 1400 depicts three curves: a measured value, a breath rate corrected value, and an actual value. The actual value may represent a gas concentration at the inlet to a breath sampling apparatus. The measured value may represent a gas concentration measured at another point in the breath sampling apparatus, such as an outlet. The breath rate corrected value may represent the measured value of the gas concentration after it has been adjusted. To generate graph 1400, four measurements of gas concentration may be taken for four breath rates: 10 bpm, 30 bpm, 40 bpm, and 60 bpm. As graph 1400 illustrates, the breath rate corrected value approximates or matches the actual value. The breath rate may be corrected using one or more breath rate correction factor equations.

Table 1420 in FIG. 14B provides some exemplary breath rate correction factor equations. Each equation relates the measured gas concentration (y) to the breath rate (x). In one variation, the breath rate correction factor equation is linear. In further variations, the breath rate correction factor comprises multiple linear equations, with each equation providing a correction for a specific range of breath rates. Using different ranges may improve the fidelity of the correction. In another variation, the breath rate correction factor equation is a quadratic equation. In further variations, multiple quadratic equations may be used for multiple breath rate ranges.

In some variations, the coefficients of a linear or quadratic equation are determined by using a breath simulator. In such variations, the breath simulator provides a known concentration of a gas at the inlet to a breath sampling apparatus at a known breath rate. From the breath rate and the deviation of measured gas concentration at another location of the sampling apparatus from known gas concentration at the inlet, a rate factor equation is derived by fitting the measurements to an equation. For example, the embodiment depicted in FIG. 14A may provide a deviation for each discrete breath rate. The deviation at each breath rate can be extrapolated to produce one or more equations spanning the operating range. In this way, a measured gas concentration can be corrected to approximate an actual gas concentration for any breath rate within the operating range.

Further variations may provide adjustments for a range of measured gas concentrations to a range of corrected gas concentrations over a range of breath rates. In one variation, a method for deriving a breath rate correction equation may include deriving multiple polynomial equations that span the ranges of measured gas concentrations, actual gas concentrations, and breath rates and utilizing the polynomial equations to populate a look-up table. In other variations, an apparatus may include a processor that references a look-up table to determine a polynomial equation for a given breath rate, where the polynomial equation provides a corrected gas concentration for a measured gas concentration at the given breath rate. In this way, variations of the present disclosure may beneficially provide for determining a gas concentration in a patient's breath independently of patient cooperation. That is, the gas concentration may be determined for patients who are unwilling or unable to regulate their breathing to correlate to a "normal" breathing pattern.

Figure 15A:
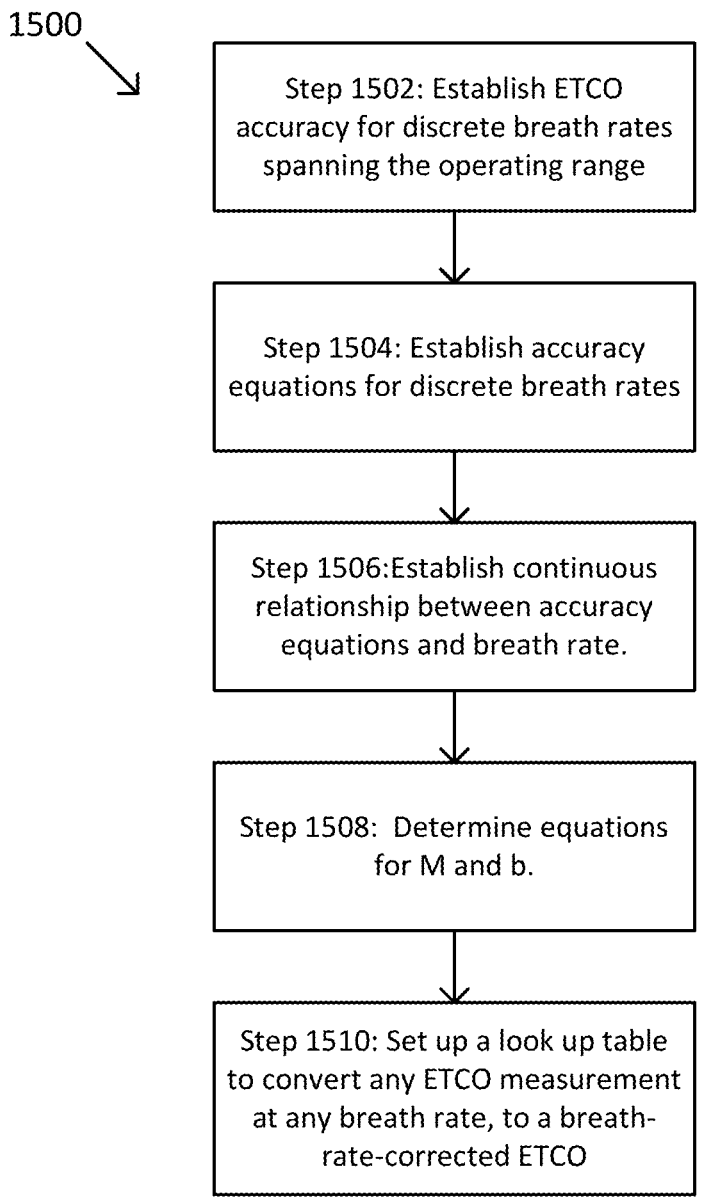
FIG. 15A illustrates a method for creating a look-up table to convert measured ETCO at a given breath rate to a corrected ETCO.

FIG. 15A illustrates method 1500 for creating a look-up table to convert measured ETCO at a given breath rate to a corrected ETCO, in accordance with one variation. The method may begin by establishing ETCO accuracy for discrete breath rates and for discrete known gas concentrations (step 1502). In the variation shown in FIG. 15A, the discrete breath rates and gas concentrations are taken to span an operating range, but it should be understood that the discrete breath rates or gas concentrations need not span the entire range. In some variations, the discrete breath rates may cover a subset of the operating range and the method may extrapolate that subset to a broader range, if necessary. For example, a look-up table covering an operating range of 8 bpm to 60 bpm may, in one variation, be populated by taking measurements at 10 bpm, 30 bpm, and 50 bpm.

Although ETCO is specifically discussed with respect to FIGS. 15A-E, the disclosure is not limited to ETCO. In other variations, the methods described herein may be applied to other gases and/or breath stages and multiple gas concentrations. Other influencing variables may also be included in the database creation, such as different operating temperatures, different secondary gas levels, or the like.

In some embodiments, the look-up table may be populated by drawing a known ETCO through an inlet of an apparatus and then measuring the ETCO at another point in the apparatus. The procedure may be repeated for multiple breath rates.

Figure 15B:
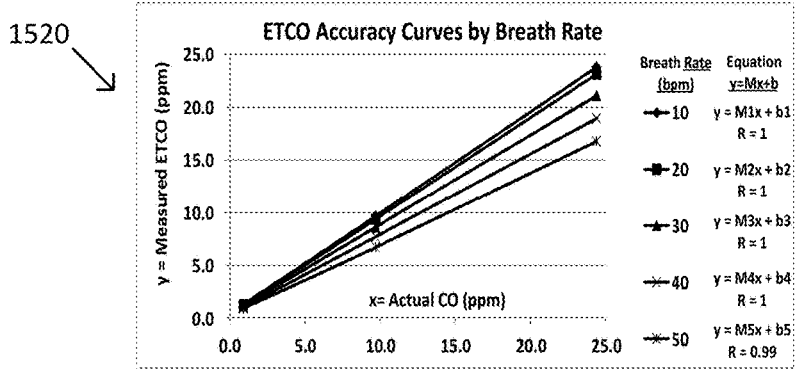
FIG. 15B provides a graph of ETCO accuracy.

A specific variation of establishing ETCO accuracy, such as in step 1502, is depicted in graph 1520 of FIG. 15B. Graph 1520 illustrates a measured gas concentration (y axis, "Measured ETCO") for three known CO concentrations (x axis, "Actual CO"). The measurements are repeated across five breath rates: 10 bpm, 20 bpm, 30 bpm, 40 bpm, and 50 bpm; and at three gas concentrations: 0.91 ppm, 9.70 ppm and 24.4 ppm. Although the variation of FIG. 15B shows five specific breath rates and three gas concentrations, other variations may use a different number and/or different rates and concentrations.

Returning to FIG. 15A, method 1500 continues with step 1504. At this step, accuracy equations for discrete breaths are established. As used herein, "an accuracy equation" can be understood to be a polynomial equation that fits the measured gas concentrations to actual gas concentrations of a breath rate, wherein data "fits" an equation when the data is interpolated, extrapolated, or smoothed. The equation need not correlate with the data correctly and may approximate the data. The degree of approximation may be determined by the requirements of a specific application.

In some variations, non-polynomial equations may be used to describe the relationships, such as logarithmic equations, exponential equations, or other equations. Specific accuracy equations are illustrated in graph 1520 of FIG. 15B. For each of the breath rates, a linear equation is derived that approximates "Actual CO" to "Measured ETCO" across all "Actual CO" concentrations. The linear equation is derived by fitting the known CO concentrations and measured ETCO concentrations for each breath rate.

Although the variation in FIG. 15B illustrates a linear equation, other variations may include polynomial equations of higher orders. For example second, third, and fourth order polynomial equations. In some variations, the maximum order may be one less than the number of measurements taken. For example, three measurements were taken in the embodiment illustrated in FIG. 15B and so the maximum order for the polynomial equation may be two (i.e., a quadratic equation). In FIG. 15B, the measurements resulted in a linear equation, but need not have. However, a linear equation may be beneficial because it may require less computing resources to solve. In some variations, the measurements may be fit to an equation of less than the maximum order. In such variations, it may be beneficial to fit the measurements to a "best-fit" equation of a lower order to reduce the need for computing resources.

Referring again to FIG. 15A, method 1500 then moves to step 1506 and establishes a continuous relationship between the accuracy equations and breath rate. In this step, the coefficients are collated by the order in each of the breath rate accuracy equations. For each order, the coefficients for that order and each coefficient's corresponding breath rate is used to determine the continuous relationship.

Figure 15C:
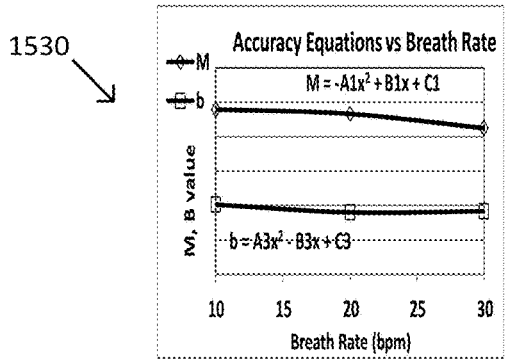
FIG. 15C provides a graph comparing slope and offset to breath rate.
Figure 15D:
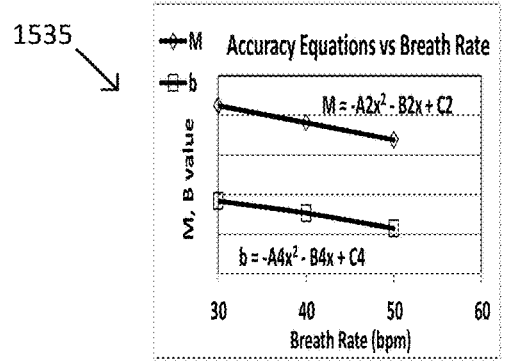
FIG. 15D provides a graph comparing slope and offset to breath rate.

FIGS. 15C and 15D illustrate two such comparisons. FIG. 15C illustrates graph 1530 which plots the slope (M) and offset (b) of the linear accuracy equations with the discrete breath rates between 10 and 30. Similarly, FIG. 15D illustrates graph 1535 which plots the slope and offset of the linear accuracy equations with the discrete breath rates between 30 and 50. Two separate ranges may allow for lower order equations to be derived for the coefficients, thereby reducing the amount of computer resources necessary to solve the equations. Further, by reducing the breath rates to two separate ranges, the fidelity of the system may be improved. For example, FIGS. 15C and 15D illustrate two equations which have a constant second derivative. A higher order polynomial equation may result in a non-constant second derivative, thereby resulting in possible wide variances in the region of a measured concentration.

Although FIGS. 15C and 15D depict a separation of the breath rates into two ranges, other variations may not separate the breath rates into ranges. Other variations may separate the breath rates into three, four, or five, or more than five ranges.

Returning to FIG. 15A, method 1500 continues with determining equations for the slope and offset of the accuracy equations based on the continuous relationship established, step 1508. In some embodiments, steps 1506 and 1508 may be performed at the same time, that is, determining the relationships between the continuous relationship may result in determining the slope and offset equations. FIGS. 15C and 15D illustrate quadratic equations derived from the relationship between the coefficients of the accuracy equations and the breath rates. Each of the quadratic equations in FIGS. 15C and 15D has a coefficient at each order (which may include a coefficient=0 in some variations). These coefficients are used in the next step of method 1500.

Although FIGS. 15C and 15D illustrate quadratic equations, polynomial equations of other orders may be used. For example, first order (linear), third order, fourth order, fifth order, sixth order, or higher order polynomial equations could be used. The maximum order of the polynomial equations may be the number of discrete breath rates minus one. As in FIGS. 15C and D, the polynomial equations could comprise lower orders than the maximum orders. This may improve fidelity if some discrete regions of the curve can represent a lower order curve. This may also reduce the use of computing resources because the difficulty of solving a polynomial equation increases as the order increases.

Returning again to FIG. 15A, Step 1510 sets up a look table based on the coefficient equations determined in the previous step. Referring now to the exemplary embodiment in FIG. 15E, the look up table can be found on the bottom of Table 1540. For a given breath rate (less than or equal 30 or greater than 30), coefficients for each order of quadratic equation can be identified. There are two equations derived for each of slope and for offset. Because slope and offset are determined by quadratic equations in FIGS. 15A-E, the look-up table includes three coefficients for each of slope and offset at each breath rate.

Figure 15E:
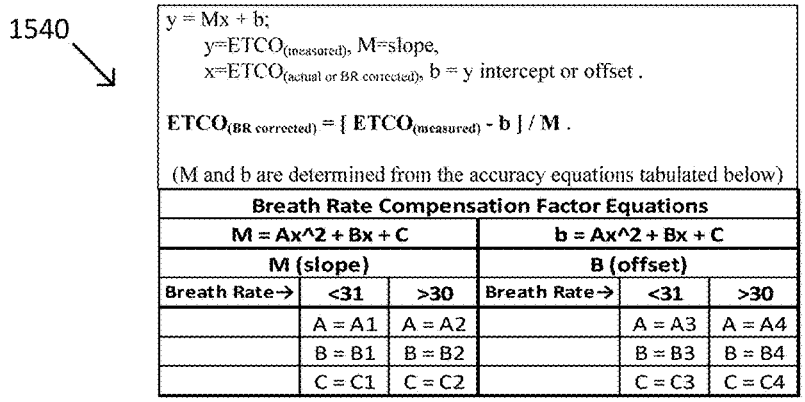
FIG. 15E provides a look-up table and some exemplary compensation equations.

FIG. 15E also provides one variation of correcting a measured gas concentration. Once a breath rate is determined, the relevant coefficients are determined. Once the relevant coefficients are determined, the equations for slope and offset can be determined. Using the breath rate, actual values for slope and offset can be determined. These values are then used to calculate the corrected concentration using the following formula:

$$ETCO_{(BR\ Corrected)} = [ETCO_{(Measured)} - b]/M$$

It should be understood that the above equation may vary if the number of coefficients of the accuracy equation is varied. For example, the variation of FIG. 15E had two coefficients. Thus, the above equation results from solving a linear equation (two coefficients). If more coefficients are used, then a solution to a higher order equation may be necessary. The solution may be obtained using any mathematical technique capable of solving for an unknown variable in a higher order equation.

When the apparatus is in use, should the measured breath rate or measured gas concentration be outside of the ranges defined by the above procedure, the apparatus may react in a variety of ways, depending on the details of the clinical application. The apparatus may not compute a corrected ETCO result and notify the user that the measured parameters are outside of the apparatus's range. The apparatus may compute the corrected ETCO despite being out of range, and provide the result to the user while notifying the user that the accuracy of the result may be less accurate because the measured parameters are outside of the operating range. In some variations, the apparatus may simply compute a result by extrapolating with the appropriate equations. In this way, variations of the present disclosure may beneficially provide for determining a gas concentration in a patient's breath independently of patient cooperation. That is, the gas concentration may be determined for patients who are unwilling or unable to regulate their breathing to correlate to a "normal" breathing pattern.

In some variations, the entire set of values within an operating range may be tested in advance, and a look-up database created based on the results. For example, breath rates of 10, 11, 12 and so on to 50 bpm (for example), at gas concentrations of 1.0, 1.1, 1.2 and so on to 25.0 ppm can be pre-tested. When the device is in use, the corrected gas concentration can be obtained by finding the appropriate value in the database for the measured breath rate and measured gas concentration. In some variations, a combined approach is used such as pre-testing all breath rates but only a set of discrete gas concentrations within or near the operating range.

While the above embodiment describes the use of breath rate as the breathing pattern parameter used in the corrections, it is understood that rather than breath rate, the same embodiment may be accomplished with any breathing pattern related parameter. Examples of other parameters include expiratory time, end-tidal time, inspiratory time, inspiratory:expiratory ratio, tidal volume, minute volume, airway pressure amplitude, capnometry signal amplitude, and the duration of the positive slope of the capnometry signal.

In some variations, a method of determining a gas concentration at the inlet of an apparatus may include determining the patient's breath rate and measuring the concentration of the patient's breath somewhere else in the apparatus. As used herein, measured a gas in an apparatus can be understood to mean measuring anywhere within the apparatus, such as at an outlet or an interior point in the apparatus, such as in a tube or compartment. With the measured gas concentration, a database can be accessed to obtain a plurality of coefficients corresponding to the patient's breath rate. In the example of FIG. 15E, the plurality of coefficients are separated by breath rate into two regions: at or below 30 bpm, or at or above 30 bpm. Other variations may arrange the coefficient's differently. Once the coefficients are obtained, the method may derive a first plurality of polynomial equations (in FIG. 15A-E, the first polynomial equations are quadratic). These equations provide coefficients for second plurality of equations (in FIG. 15A-E, the second polynomial equations are linear), where the coefficients are then used to form a compensation equation (in FIG. 15A-E, the compensation equation is linear). The compensation equation is then used to adjust the measured gas concentration to determine the gas concentration at the inlet.

In some variations, an apparatus may include a processor for carrying out the above method of determining a gas concentration at the inlet of an apparatus. The apparatus may also include a measuring point, a gas analyzer for determining a gas concentration at the measuring point, an inlet, and a breath speed analyzer. The processor may access a database stored on a non-transitory computer readable medium, where the database includes a plurality of coefficients for each breath rate in the operating range.

In some variations, a sampling system may be tuned for an upper limit breath rate. For a given sample volume (sample volume may be determined to meet specifications of a particular application), the flow rate of a flow generator, such as a pump, may be configured to fill the entire sample volume with end-tidal gas for the upper limit breath rate. For breath rates lower than the upper limit breath rate, the sample volume is completely filled with end-tidal gas, albeit not all of the end-tidal gas for that breath. In further variations, the system may include an upper limit cut-off that limits sampling to breaths at or below the upper limit. In this way, these variations may beneficially prevent non-end-tidal gas from entering the sample volume. Thus, variations of the present disclosure may beneficially provide for determining a gas concentration in a patient's breath independently of patient cooperation. That is, the gas concentration may be determined for patients who are unwilling or unable to regulate their breathing to correlate to a "normal" breathing pattern.

In some variations, a gas sampling flow rate may be determined to fit the requirements of a particular application. For example, an upper limit for normal breathing may be described by a breath frequency parameter, such as 60 bpm. However, for certain patients (such as neonates, for example), a normal breath rate may exceed 60 bpm. In such an instance, the upper limit may be higher, such as at 100 bpm. Similarly, the sample volume may be chosen to reflect the needs of a particular application. In some variations, other frequency parameters may be chosen, such as inspiratory time, breath period, expiratory time, end-tidal time, capnometer signal rise duration, or another parameter that describes at least a portion of the patient's breathing. In some variations, an instantaneous carbon monoxide sensor is used.

Figure 16A:
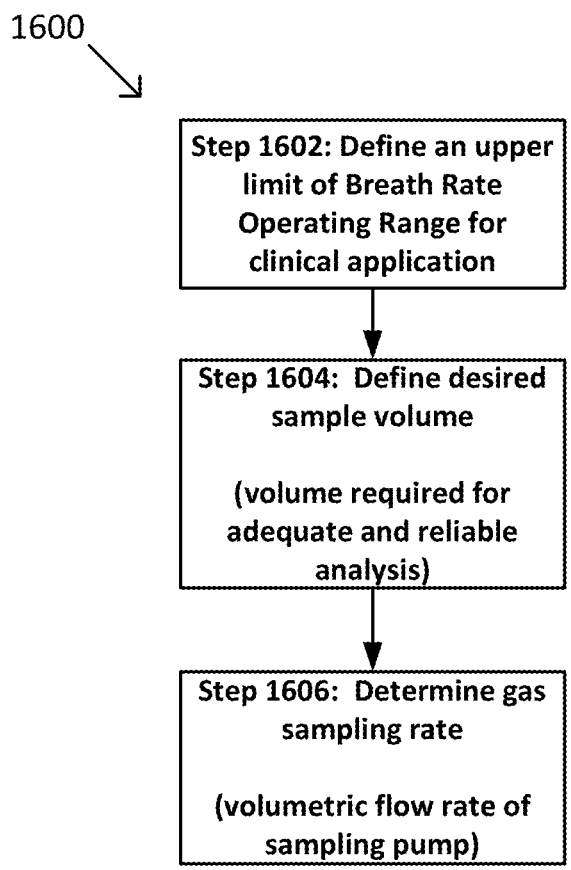
FIG. 16A illustrates a method of determining a gas sampling rate of a flow generator to correlate to an upper limit breath rate and predetermined sampling volume.

FIG. 16A illustrates method 1600 of determining a gas sampling rate of a flow generator to correlate to an upper limit breath rate and predetermined sampling volume. Method 1600 begins with step 1602: defining an upper limit for the breath rate (BR). As discussed above, the upper limit may be determined to meet the requirements of a specific application.

Method 1600 continues with step 1604, defining a desired sample volume (V(s)). In the variation of method 1600, the sample volume is sized for adequate and reliable analysis. In other variations, the sample volume may be sized to factor in other considerations.

Method 1600 continues with step 1606, determining the gas sampling flow rate (Q(S)). In the variation of method 1600, the flow generator is a pump, but other flow generators could be used, such as the examples described herein. The gas sampling flow rate may be calculated to fill the desired sample volume at the upper limit breath rate.

In some variations, the sampling flow rate is calculated from the following equation $Q(S)=T_{ET}/V(S)$, wherein $T_{ET}$ is the estimated end-tidal period and is a function of the breath rate. In some variations, $T_{ET}$ may be assumed to be half of the expiratory time, which itself may be assumed to be half of the breath period (inspiratory and expiratory periods). The breath period (seconds) is 60/breath rate. For example, if the upper limit breath rate is 60 bpm, then $T_{ET}$ may be assumed to be 0.25 seconds. If the sample volume in this example is 0.5 ml, then the sampling flow rate is 2 ml per second.

Figure 16B:
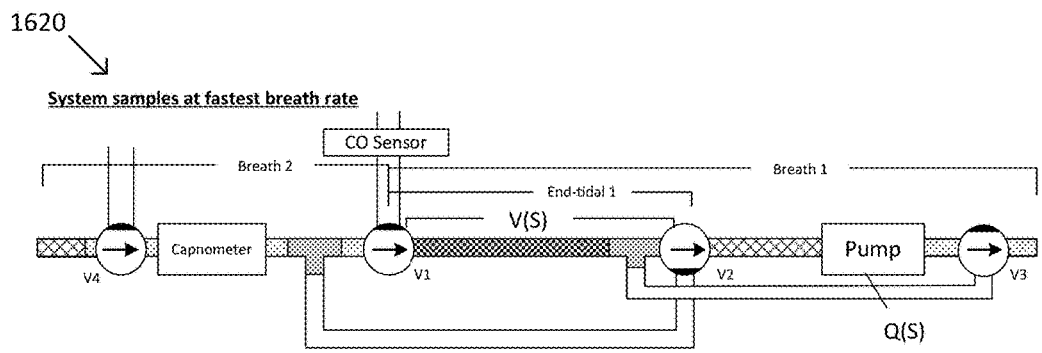
FIG. 16B illustrates the pneumatic gas capture system of FIG. 5A or 5B drawing a patient's breath at an upper limit breath rate.

FIG. 16B illustrates the pneumatic gas capture system of FIG. 5A or 5B in configuration 1620. Configuration 1620 includes the gas sampling rate of the pump configured for an upper limit breath rate, and where the patient's breath rate is at the upper limit. As can be seen in FIG. 16B, the sample volume is entirely filled with end-tidal gas and there is no en-tidal gas outside of the sample volume.

Figure 16C:
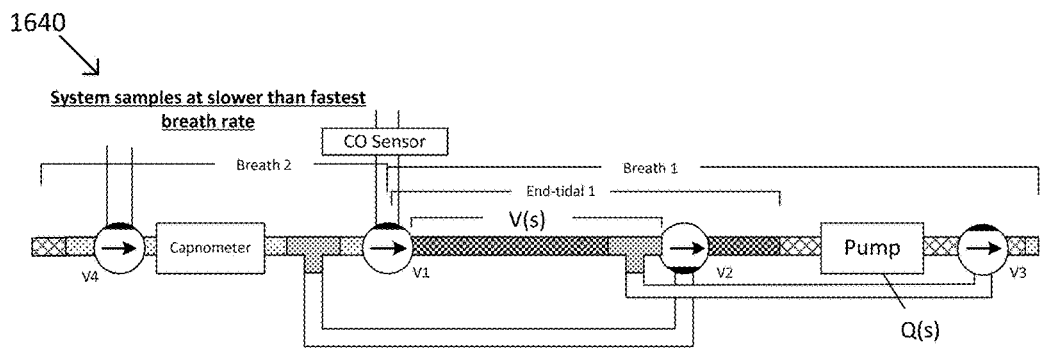
FIG. 16C illustrates the pneumatic gas capture system of FIG. 5A or 5B drawing a patient's breath at a breath rate below an upper limit breath rate.

FIG. 16C illustrates the pneumatic gas capture system of FIG. 5A or 5B in configuration 1640. Configuration 1640 includes the gas sampling rate of the pump configured for an upper limit breath rate, and where the patients' breath rate is below the upper limit. As can be seen in FIG. 16C, the sample volume is entirely filled with end-tidal gas, but there is end-tidal gas from the breath outside of the sample volume. FIG. 16C illustrates the end-tidal gas outside of the sample volume as located downstream (to the right) of V2. However, in other embodiments, the end-tidal gas outside of the sample volume may be located upstream (to the left) of V1, or a combination of upstream of V1 or downstream of V2. In this way, variations of the present disclosure may beneficially provide for determining a gas concentration in a patient's breath independently of patient cooperation. That is, the gas concentration may be determined for patients who are unwilling or unable to regulate their breathing to correlate to a "normal" breathing pattern.

Some variations include elements and functionality from individual variations described above, that is, some variations may combine different elements of the different variations described above. For example, a user interface of the apparatus may allow the user to enter a certain patient parameter, such as a patient type, for example adult or infant, or for example premature neonate or full term infant. The control system of the apparatus will select a preferred breath rate compensation methodology, selected from the embodiments described above, and use that methodology accordingly. In some variations, the apparatus may, for example, use the embodiment described in FIG. 16 in which the system is tuned for a breath rate of 60 bpm, therefore collecting an undiluted end-tidal sample for any breath rate at or below 60 bpm and therefore not requiring breath rate compensation. The variation may further allow for collection of breath rates above 60 bpm, where a breath rate compensation algorithm is invoked. The breath rate compensation algorithm could for example be the collection of end-tidal gas from two breaths in order to fill the sample tube such as described in relation to FIGS. 10A-11F, or can be the use of a polynomial equation correction factor such as described in relation to FIGS. 15A-15E.

In the foregoing descriptions of variations of the invention, the examples provided are illustrative of the principles of the invention, and that various modifications, alterations, and combinations can be made by those skilled in the art without departing from the scope and spirit of the invention. Any of the variations of the various breath measurement and sampling devices disclosed herein can include features described by any other breath measurement and sampling devices or combination of breath measurement and sampling devices herein. Accordingly, it is not intended that the invention be limited, except as by the appended claims. For all of the variations described above, the steps of the methods need not be performed sequentially.

What is claimed is:

1. An apparatus for analyzing a gas concentration in a breath of a patient, the apparatus comprising:
   a sample compartment that captures the breath;
   a breath analyzer that determines a breath rate of the patient;
   a gas analyzer that determines a gas concentration of the breath in the sample compartment, wherein the gas concentration comprises one selected from the group consisting of a carbon monoxide concentration and a carbon dioxide concentration;
   a processor comprising an algorithm that determines a degree of non-homogeneity of the breath sample in the sample compartment based on the breath rate of the patient, wherein the algorithm further determines a corrected gas concentration based on the breath rate of the patient, the degree of non-homogeneity, and the determined gas concentration; and
   an output device that communicates the corrected gas concentration.

2. The apparatus of claim 1, further comprising a flow control pump which draws breath through the sample compartment.

3. The apparatus of claim 1, wherein the breath analyzer determines at least one of a start or an end of a sub-portion of the patient's breath.

4. The apparatus of claim 3, further comprising a valve on at least one of an inlet and an outlet of the sample compartment, and wherein the sub-portion of the patient's breath is isolated by controlling the valve based on the start or the end of the sub-portion of the patient's breath.

5. A method of analyzing a gas concentration in a breath of a patient comprising:
   capturing the breath in a sample compartment;
   determining a breath rate of the patient using a breath analyzer;
   determining a gas concentration of the breath in the sample compartment using a gas analyzer, wherein the gas concentration comprises one selected from the group consisting of a carbon monoxide concentration and a carbon dioxide concentration; and executing instructions from a processor for
   determining a degree of non-homogeneity of the breath in the sample compartment based on the breath rate of the patient;
   determining a corrected gas concentration based on the breath rate of the patient, the degree of non-homogeneity, and the determined gas concentration; and
   communicating the corrected gas concentration to an output device.

6. The method of claim 5, further comprising drawing breath through the sample compartment with a flow control pump.

7. The method of claim 5, further comprising determining at least one of a start or an end of a sub-portion of the patient's breath using the breath analyzer.

8. The method of claim 7, further comprising isolating a sub-portion of the breath in the sample compartment based on at least one of the start or the end of the sub-portion of the patient's breath.

* * * * *